(12) United States Patent
Jeong et al.

(10) Patent No.: US 10,206,573 B2
(45) Date of Patent: Feb. 19, 2019

(54) METHOD OF OBTAINING BIOMETRIC INFORMATION IN ELECTRONIC DEVICE AND ELECTRONIC DEVICE FOR THE SAME

(71) Applicant: Samsung Electronics Co., Ltd., Gyeonggi-do (KR)

(72) Inventors: Injo Jeong, Gyeonggi-do (KR); Jeahyuck Lee, Gyeonggi-do (KR); Younghwan Kim, Gyeonggi-do (KR); Seungeun Lee, Seoul (KR); Yongjin Lee, Seoul (KR); Bokun Choi, Seoul (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 0 days.

(21) Appl. No.: 15/896,434

(22) Filed: Feb. 14, 2018

(65) Prior Publication Data
US 2018/0235471 A1 Aug. 23, 2018

(30) Foreign Application Priority Data
Feb. 23, 2017 (KR) .......................... 10-2017-0024384

(51) Int. Cl.
| | |
|---|---|
| *G08B 1/00* | (2006.01) |
| *A61B 5/00* | (2006.01) |
| *A61B 5/11* | (2006.01) |
| *A61B 5/0205* | (2006.01) |
| *G06K 9/00* | (2006.01) |

(52) U.S. Cl.
CPC .......... *A61B 5/0026* (2013.01); *A61B 5/0006* (2013.01); *A61B 5/0205* (2013.01); *A61B 5/1116* (2013.01); *A61B 5/1118* (2013.01); *A61B 5/746* (2013.01); *G06K 9/00013* (2013.01); *G06K 9/00335* (2013.01)

(58) Field of Classification Search
CPC ..... A61B 5/0026; A61B 5/006; A61B 5/1116; A61B 5/1118
USPC ............... 340/539.1, 539.11, 539.13, 539.12
See application file for complete search history.

(56) References Cited

U.S. PATENT DOCUMENTS

| | | |
|---|---|---|
| 6,062,216 A | 5/2000 | Corn |
| 2008/0009685 A1 | 1/2008 | Kim et al. |
| 2008/0157956 A1 | 7/2008 | Radivojevic et al. |
| 2009/0203972 A1 | 8/2009 | Heneghan et al. |
| 2011/0178377 A1 | 7/2011 | Heneghan et al. |

(Continued)

OTHER PUBLICATIONS

International Search Report dated May 30, 2018.

*Primary Examiner* — Daryl Pope
(74) *Attorney, Agent, or Firm* — Cha & Reiter, LLC

(57) ABSTRACT

An electronic device and method are disclosed herein. The electronic device includes an image sensor, a radio frequency (RF) sensor, and a processor. The processor implements the method, including capturing an image including at least one object using an image sensor, determining an interest area of the at least one object included within the captured image, transmitting a radio frequency (RF) signal to at least a portion of the interest area using an RF sensor, receiving the transmitted RF signal reflected from the at least the portion of the interest area using the RF sensor, and obtaining biometric information for the at least one object based on the reflected RF signal.

20 Claims, 22 Drawing Sheets

(56) References Cited

U.S. PATENT DOCUMENTS

| | | | |
|---|---|---|---|
| 2014/0005547 A1* | 1/2014 | Balasubramanian | A61B 8/145 |
| | | | 600/447 |
| 2014/0176346 A1 | 6/2014 | Brumback et al. | |
| 2016/0058366 A1 | 3/2016 | Choi et al. | |
| 2016/0310046 A1 | 10/2016 | Heinrich et al. | |
| 2017/0128040 A1* | 5/2017 | Kim | A61B 8/14 |

* cited by examiner

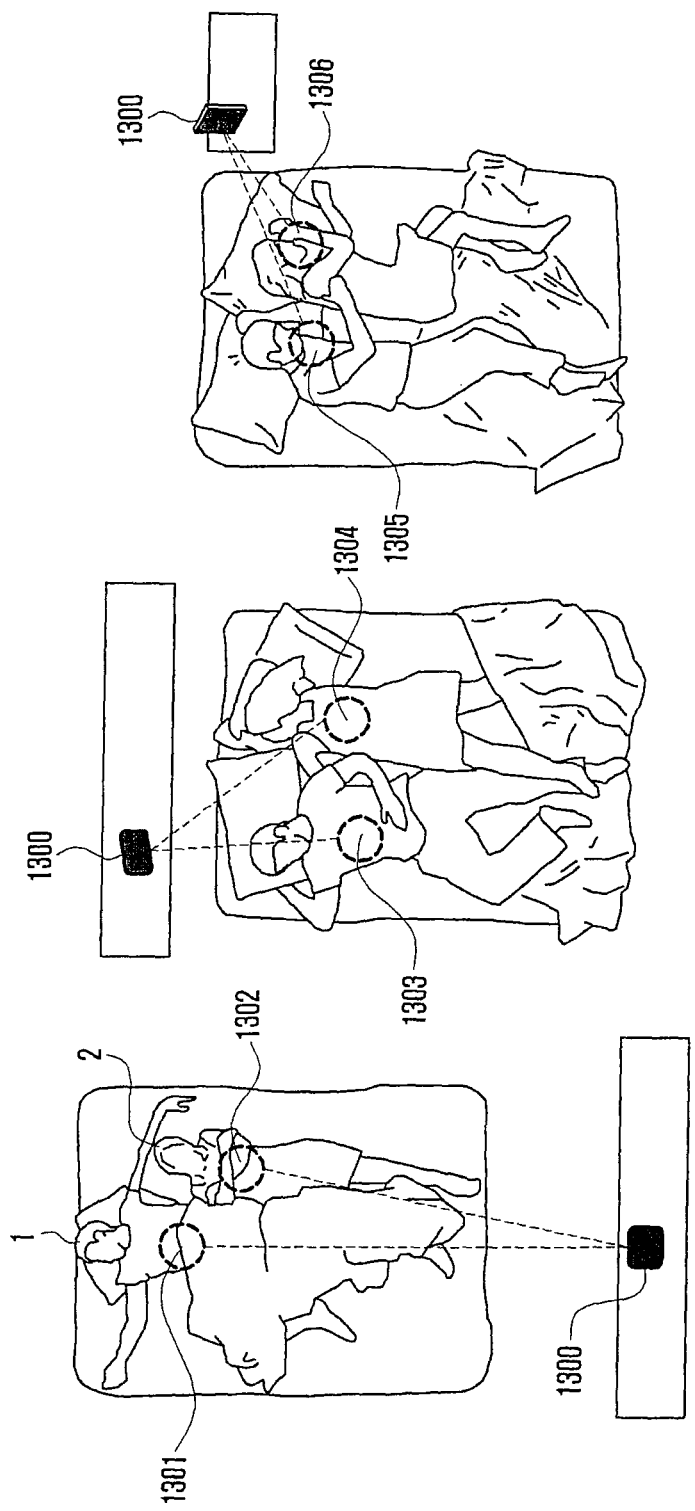

METHOD OF OBTAINING BIOMETRIC INFORMATION IN ELECTRONIC DEVICE AND ELECTRONIC DEVICE FOR THE SAME

CROSS-REFERENCE TO RELATED APPLICATION(S)

This application is based on and claims priority under 35 U.S.C. § 119 to Korean Patent Application No. 10-2017-0024384, filed on Feb. 23, 2017, in the Korean Intellectual Property Office, the disclosure of which is incorporated by reference herein in its entirety.

TECHNICAL FIELD

The present disclosure relates to a method of obtaining biometric information about an object and an electronic device for the same and, more particularly, to a method of obtaining biometric information about a user using an electronic device and the electronic device for the same.

BACKGROUND

Electronic devices that autonomously or remotely monitor a user have been appearing gradually in the market.

A monitoring result of an electronic device may be used for various purposes. For example, the electronic device may provide a service most appropriate to a current state of a user or may notify a user of an emergency situation to others to protect the safety of the user.

A device that monitors a user may include, for example, a voice recognition device. The voice recognition device may recognize a user voice and provide various services according to a voice recognition result. For example, the voice recognition device may induce a natural conversation with a user to determine a user feeling or mood. The voice recognition device may provide a music service in consideration of a user feeling or mood or may provide a service such as a personal assistant that notifies an alarm/schedule/weather condition.

Further, the voice recognition device may be interworked with a peripheral smart home device to adjust lighting of a smart bulb to correspond to a user feeling or may control a smart heating regulator to adjust a room temperature. Generally, it is beneficial for a voice recognition device that monitors a user to be located at a short distance from the user in order to recognize the user's voice.

As a device for monitoring a user, a camera may be used. In this case, in order to accurately recognize a user state, image analysis technology of a high specification may be utilized; thus, high power consumption may result. Further, leaked exposure of a photograph of a user may result in a serious loss of user privacy.

SUMMARY

The present disclosure has been made in view of the above problems and provides a method of obtaining biometric information about an object and an electronic device for the same that accurately monitors a user state by overcoming an existing user monitoring problem and provides various services according to a monitoring result.

The technical problem of the present disclosure is not limited to the above-described technical problems and other technical problems will be understood by those skilled in the art from the following description.

In accordance with an aspect of the present disclosure, an electronic device is disclosed including an image sensor, a radio frequency (RF) sensor including a transmitting circuit and a receiving circuit, and a processor configured to: capture an image including at least one object using the image sensor, determine an interest area of the at least one object included within the captured image, transmit an RF signal to at least a portion of the interest area using the transmitting circuit, receive the transmitted RF signal when the transmitted RF signal is reflected from the at least the portion of the interest area using the receiving circuit, and obtain biometric information for the at least one object based on the reflected RF signal.

In accordance with another aspect of the present disclosure, a method in an electronic device is disclosed including: capturing an image including at least one object using an image sensor, determining an interest area of the at least one object included within the captured image, transmitting a radio frequency (RF) signal to at least a portion of the interest area using an RF sensor, receiving the transmitted RF signal reflected from the at least the portion of the interest area using the RF sensor, and obtaining biometric information for the at least one object based on the reflected RF signal.

In accordance with another aspect of the present disclosure, a non-transitory computer readable recording medium comprising instructions executable by a processor to cause the processor to perform operations including: capturing an image including at least one object using an image sensor, determining an interest area of the at least one object included within the captured image, transmitting a radio frequency (RF) signal to at least a portion of the interest area using an RF sensor, receiving the transmitted RF signal reflected from the at least the portion of the interest area using the RF sensor, and obtaining biometric information for the at least one object based on the reflected RF signal.

BRIEF DESCRIPTION OF THE DRAWINGS

The objects and features of the present disclosure will be more apparent from the following detailed description in conjunction with the accompanying drawings, in which:

FIG. 13A, FIG. 13B and FIG. 13C are diagrams illustrating a use process of an electronic device that monitors a user sleep state according to an example embodiment of the present disclosure;

DETAILED DESCRIPTION EXAMPLE

Figure 1:
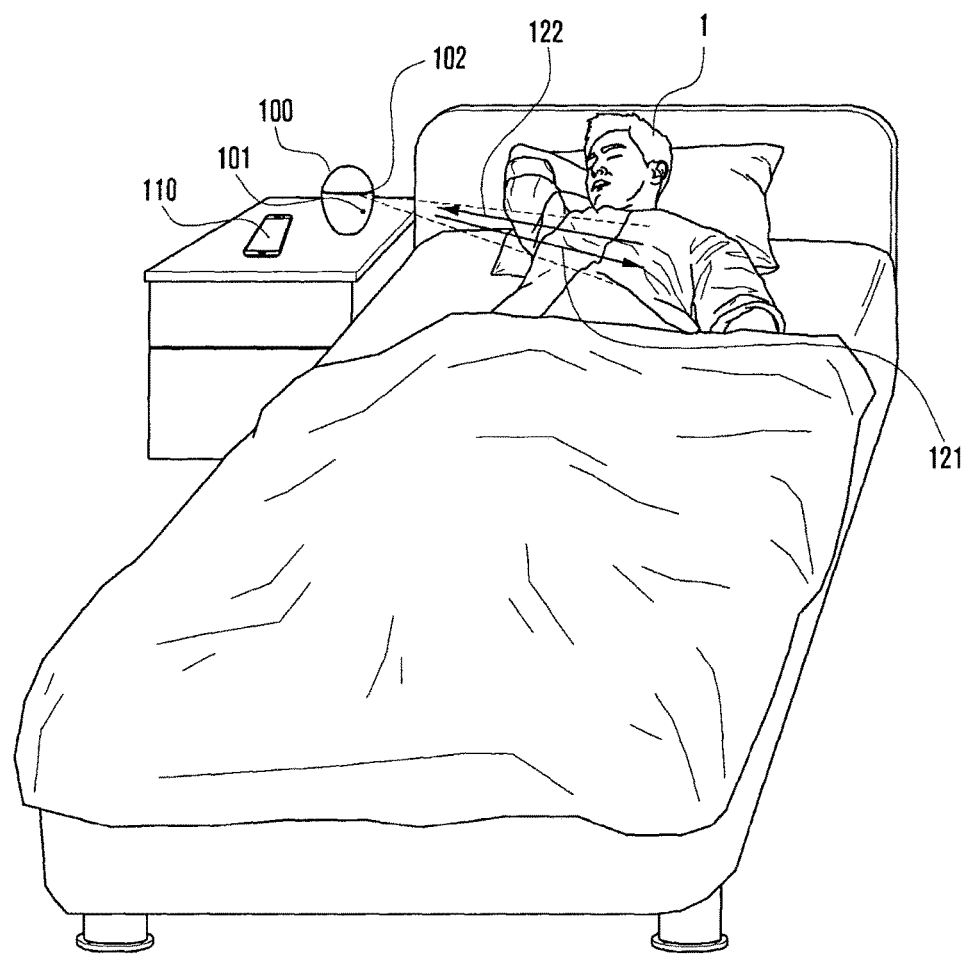
FIG. 1 is a diagram illustrating a use environment of an electronic device according to an example embodiment of the present disclosure.

Hereinafter, various example embodiments of this document will be described in detail with reference to the accompanying drawings. It should be understood that example embodiments and terms used in the example embodiments do not limit technology described in this document to a specific embodiment and include various changes, equivalents, and/or replacements of a corresponding example embodiment. The same reference numbers are used throughout the drawings to refer to the same or like parts. Unless the context otherwise clearly indicates, words used in the singular include the plural, the plural includes the singular. In this document, an expression such as "A or B" and "at least one of A or/and B" may include all possible combinations of the together listed items. An expression such as "first" and "second" used in this document may indicate corresponding constituent elements regardless of order and/or importance, and such an expression is used for distinguishing a constituent element from another constituent element and does not limit corresponding constituent elements. When it is described that a constituent element (e.g., a first constituent element) is "(functionally or communicatively) coupled to" or is "connected to" another constituent element (e.g., a second constituent element), it should be understood that the constituent element may be directly connected to the other constituent element or may be connected to the other constituent element through another constituent element (e.g., a third constituent element).

In this document, "configured to (or set to)" may be interchangeably used in hardware and software with, for example, "appropriate to", "having a capability to", "changed to", "made to", "capable of", or "designed to" according to a situation. In any situation, an expression "device configured to" may mean that the device is "capable of" being configured together with another device or component. For example, a phrase "processor configured to (or set to) perform A, B, and C" may mean an exclusive processor (e.g., an embedded processor) for performing a corresponding operation or a generic-purpose processor (e.g., CPU or application processor) that can perform a corresponding operation by executing at least one software program stored at a memory device.

An electronic device according to various example embodiments of this document may include at least one of, for example, a smart phone, tablet personal computer (PC), mobile phone, video phone, electronic book reader, desktop PC, laptop PC, netbook computer, workstation, server, personal digital assistant (PDA), portable multimedia player (PMP), MP3 player, medical device, camera, and wearable device. The wearable device may include at least one of an accessory type device (e.g., watch, ring, bracelet, ankle bracelet, necklace, glasses, contact lens), head-mounted-device (HMD), textile or clothing integral type device (e.g., electronic clothing), body attachment type device (e.g., skin pad or tattoo), and biological implantable circuit. In an example embodiment, the electronic device may include at least one of, for example, a television, Digital Video Disk (DVD) player, audio device, refrigerator, air-conditioner, cleaner, oven, microwave oven, washing machine, air cleaner, set-top box, home automation control panel, security control panel, media box (e.g., Samsung HomeSync™, AppleTV™, or Google TV™), game console (e.g., Xbox™, PlayStation™), electronic dictionary, electronic key, camcorder, and electronic frame.

In another example embodiment, the electronic device may include at least one of a navigation device, global navigation satellite system (GNSS), event data recorder (EDR), flight data recorder (FDR), vehicle infotainment device, ship electronic equipment (e.g., ship navigation device, gyro compass), avionics, security device, vehicle head unit, industrial or home robot, drone, automatic teller machine (ATM) of a financial institution, point of sales (POS) of store, and Internet of things (e.g., bulb, various sensors, sprinkler, fire alarm, thermostat, street light, toaster, exercise device, hot water tank, heater, boiler).

In various example embodiments, the electronic device may be flexible or may be two or more combinations of the foregoing various devices. An electronic device according to an example embodiment of this document is not limited to the foregoing devices. In this document, a term "user" may indicate a person using an electronic device or a device (e.g., artificial intelligence electronic device) using an electronic device.

Further, in this document, a term "object" is an object to be a target for obtaining biometric information and may include, for example, a person, animal, or other living thing.

FIG. 1 is a diagram illustrating a use environment of an electronic device according to an example embodiment of the present disclosure.

An electronic device 100 may monitor at least one object 1.

When the object 1 is a user in sleep, the electronic device 100 may be used for monitoring a user sleep state. In this case, the electronic device 100 may be referred to as a sleep monitoring device. The electronic device 100 may remotely monitor a user without restriction of a user active state or a time.

In order to monitor the object 1, the electronic device 100 may include an image sensor 101 and a radio frequency (RF) sensor 102.

For example, the electronic device 100 may monitor a user sleep state using both the image sensor 101 and the RF sensor 102.

Specifically, the electronic device 100 may obtain image information including the object 1 using the image sensor 101. The image information may include at least one of an image and a moving picture.

The electronic device 100 may determine an interest area of the object 1 based on the obtained image information. The interest area is an area that serves as a monitoring reference region of the object 1 and may be, for example, a face, chest, back, or abdomen, but it is not limited to the foregoing examples.

When the interest area is determined, the electronic device 100 may transmit an RF signal 121 to at least a portion of the interest area using the RF sensor 102.

On receipt of an RF signal 122 reflected from at least a portion of the interest area and that corresponds to the transmitted RF signal 121, the electronic device 100 may obtain biometric information about the object 1 based on the received RF signal 122. For example, the electronic device 100 may obtain movement information according to a change of the interest area based on the received RF signal. The electronic device 100 may obtain biometric information about the object 1 based on the obtained movement information.

Specifically, the electronic device 100 may obtain movement information according to a change of a portion of a user body based on the received RF signal. More specifically, the electronic device 100 may obtain an RF signal value received at a chest surface according to a user's cardiopulmonary activity. The electronic device 100 may obtain user movement information based on an intensity difference or a phase change between a transmitted RF signal value and a received RF signal value. The electronic device 100 may obtain information about a user sleep state based the obtained movement information.

The electronic device 100 may store image information or an RF signal value of an object obtained using the image sensor 101 or the RF sensor 102, movement information obtained based on an RF signal, and biometric information obtained based on the movement information. The electronic device 100 may transmit at least a portion of the information to an external device 110 (e.g., user smart phone).

For this reason, the electronic device 100 may perform wireless or wired communication with the external device 110 and may perform short range communication. The short range communication may include, for example, BT communication, NFC communication according to NFC tagging, or Wi-Fi communication, and other detailed examples may be described later using a communication module 2220 of FIG. 22.

According to various example embodiments, the electronic device 100 may transmit the information to the external device 110 at a time set by a user, a time set to default, or a time set to predetermined periods.

The external device 110 may analyze received information to provide a sleep management service.

For example, the external device 110 may analyze received information to display sleep management information including a user sleep state or a sleep guide on a screen.

The sleep management information may be provided with a text, an image, or various type graphs. Further, the sleep management information may be provided in a hierarchical structure in which an information amount changes according to a user selection with division into a plurality of screens.

A detailed example of displaying sleep management information on a screen will be described in detail later with reference to FIGS. 14 to 16.

According to various example embodiments, in the external device 110, contents or an application related to a physical examination function or a sleep management function may be previously installed. In this case, the external device 110 may analyze information received from the electronic device 100 using the contents or application and display sleep management information as an analysis result on a screen.

According to various example embodiments, a monitoring operation of the electronic device 100 may be controlled according to the control of the external device 110. For example, when a user executes the contents or application, a monitoring request signal may be transmitted to the electronic device 100; thus, the electronic device 100 may be automatically operated.

According to various example embodiments, the electronic device 100 may directly analyze image information, an RF signal value, movement information obtained based on an RF signal, and biometric information obtained based on movement information to generate sleep management information. In this case, the sleep management information may be directly provided through an output unit (e.g., display unit, speaker) of the electronic device 100 or may be transmitted to the external device 110 such that the external device 110 provides the sleep management information.

Figure 2:
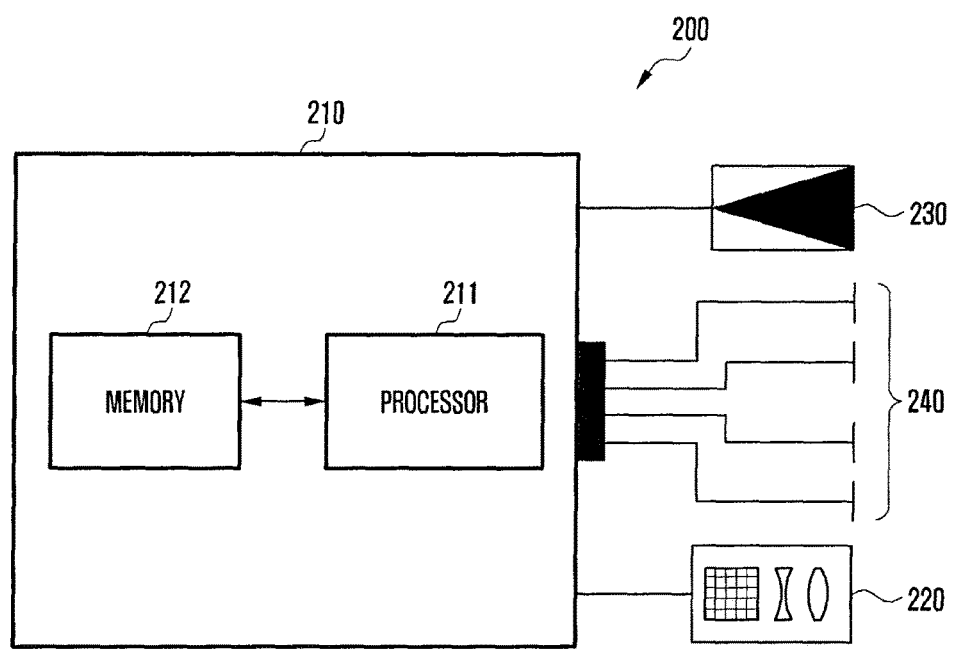
FIG. 2 is a block diagram illustrating hardware of an electronic device according to an example embodiment of the present disclosure.

FIG. 2 is a block diagram illustrating hardware of an electronic device 200 according to an example embodiment of the present disclosure.

The electronic device 200 of FIG. 2 may include a main board 210, camera 220 that photographs a subject, transmitting circuit 230 that transmits an RF signal, and receiving circuit 240 that receives a reflected RF signal.

The camera 220 includes an image sensor and may further include a general camera (or day camera) that photographs in a visible ray range as well as a night camera (e.g., infrared camera, radar camera, ultra-wide band (UWB) radar camera, or lidar camera). The night camera may recognize a user location and movement within a predetermined range to generate the user location and movement as image information.

Power applied to the camera 220 may be adjusted according to a photographing object. For example, when the electronic device 200 determines whether an object exists, low power may be applied to the camera 220. Alternatively, when the electronic device 200 determines an interest area about an object, high power may be applied to the camera 220. Alternatively, power applied to the camera 220 may be adjusted in consideration of user privacy. For example, in a situation in which consideration of user privacy is desired, low power may be applied to the camera 220.

When the electronic device 200 photographs a user in sleep, the electronic device 200 may generally use a night camera; and at a daytime, in order to obtain clear image information, the electronic device 200 may use a general camera.

The main board 210 may include a processor 211 and a memory 212.

The processor 211 may transmit an RF signal to an interest area of an object using the transmitting circuit 230 or may receive an RF signal reflected from at least a portion of an interest area that corresponds to an RF signal transmitted using the receiving circuit 240.

When the transmitting circuit 230 is configured with a plurality of transmitting antennas and when the receiving circuit 240 is configured with a plurality of receiving antennas, the processor 211 may use beamforming technology that reduces an emission angle of an antenna for an interest area. In this case, in order to enhance emission efficiency, at least one of a plurality of transmitting antennas and a plurality of receiving antennas may have a unidirectional emission pattern structure.

Further, an RF signal received by the receiving circuit 240 may be separated into various kinds of RF signals (e.g., breath related signal or heartbeat related signal) by a base band module (e.g., preprocess filter unit, amplification unit, or offset adjustment unit). The processor 211 may select a specific RF signal among separated RF signals and obtain biometric information about an object corresponding thereto. When the processor 211 obtains biometric information about an object based on a separated RF signal, a detection rate and accuracy of biometric information may be enhanced. Further, in order to enhance a detection rate and accuracy of biometric information, the processor 211 may preferentially adapt a detected RF signal to obtain biometric information about an object in a situation in which the object does not move.

Further, in order to measure heartbeat or breath of an object with a non-contact method, the transmitting circuit 230 and the receiving circuit 240 may transmit or receive an RF signal in a 3-10 GHz band. Further, the processor 211 may operate in a low power mode to control the transmitting circuit 230 and the receiving circuit 240 to transmit and receive an RF signal. In this case, a separate processor (not shown) that controls the transmitting circuit 230 and the receiving circuit 240 may be further included. While the processor 211 is in a sleep state, the separate processor (not shown) may control the transmitting circuit 230 and the receiving circuit 240.

According to various example embodiments, the processor 211 may obtain image information including at least one object using an image sensor of the camera 220. The processor 211 may determine an interest area of at least one object based on the obtained image information. In this case, when at least one object includes a first object and a second object, the processor 211 may determine each of a first interest area of the first object and a second interest area of the second object. Further, the processor 211 may determine an interest area based on at least one of a user sleep posture, a user clothing wearing state, a kind of a body portion, and a designated interest area history. Here, the interest area may include, for example, a portion of a face, chest, head, back, or abdomen as a user body portion.

When an interest area is determined, the processor 211 may transmit an RF signal to at least a portion of the interest area using the transmitting circuit 230. Further, the processor 211 may receive an RF signal reflected from at least a portion of the interest area that corresponds to the transmitted RF signal. The processor 211 may obtain biometric information about at least one object based on the received RF signal. Specifically, the processor 211 may obtain movement information according to a change of an interest area based on the received RF signal and obtain biometric information about at least one object based on the obtained movement information. Further, when a first interest area of a first object and a second interest area of a second object are determined, the processor 211 may obtain first biometric information about the first interest area and second biometric information about the second interest area. Here, biometric information about an object may include, for example, user sleep state information.

According to various example embodiments, when at least one security area is set at the memory 212, the processor 211 may store image information, a received RF signal value, movement information about an interest area obtained based on the received RF signal, or biometric information obtained based on the movement information at a security area.

According to various example embodiments, when a portion of information stored at a security area is information of a first level, the processor 211 may change the information of a first level to information of a second level of a high security level and transmit the information of a second level to an external device.

According to various example embodiments, when at least one object includes a first object and a second object and when biometric information about the first object may not be obtained, the processor 211 may re-obtain biometric information about the first object among the first object and the second object for a designated time.

According to various example embodiments, when at least one object includes a first object and a second object and when biometric information about the first object may not be obtained, the processor 211 may obtain image information including the first object using an image sensor and store the obtained image information at the memory 212.

The memory 212 may store a software program including an instruction for performing an operation and data utilized for performing the instruction according to the present disclosure.

For example, the memory 212 may include an instruction that enables the electronic device 200 to perform an operation of obtaining image information including at least one object using an image sensor, operation of determining an interest area of at least one object based on the image information, operation of transmitting an RF signal to at least a portion of an interest area using the transmitting circuit 230, operation of receiving an RF signal reflected from at least a portion of the interest area that corresponds to the transmitted RF signal using the receiving circuit 240, and operation of obtaining biometric information about at least one object based on the received RF signal.

Figure 3:
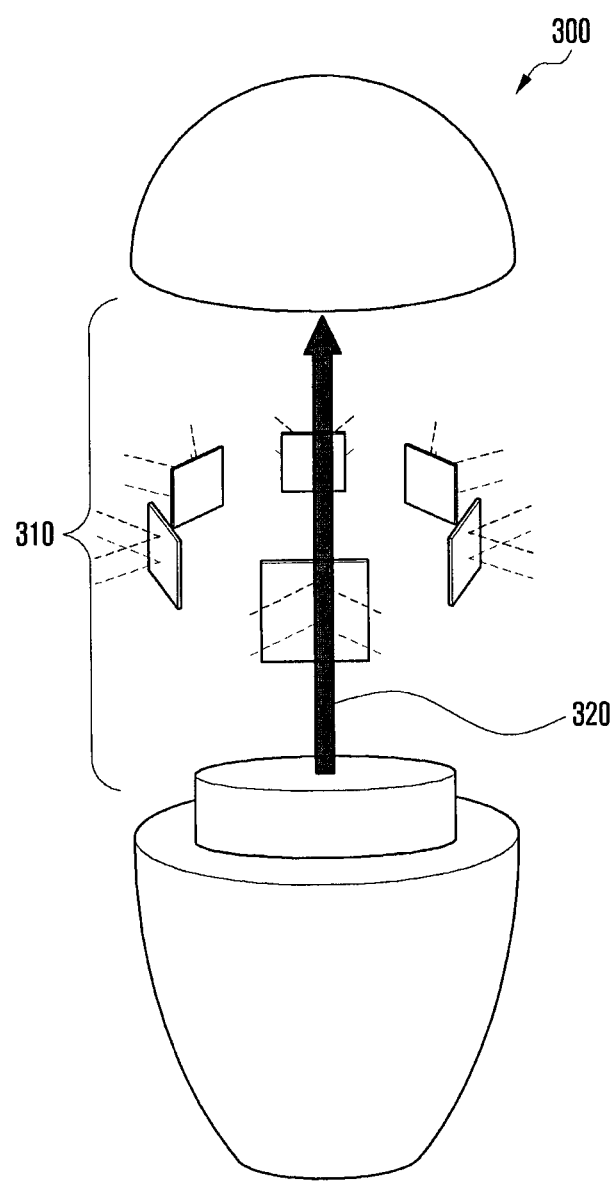
FIG. 3 is a diagram illustrating a mounting structure of an RF sensor of an electronic device according to an example embodiment of the present disclosure.

FIG. 3 is a diagram illustrating a mounting structure of an RF sensor of an electronic device according to an example embodiment of the present disclosure.

With reference to FIG. 3, an RF sensor 310 may be configured with a plurality of directional transmitting/receiving antennas. In this case, the plurality of directional transmitting/receiving antennas may be provided at a predetermined gap of 360° based on a center shaft 320 of an electronic device 300.

Accordingly, the electronic device 300 may monitor a user sleep state regardless of a direction in which the user is located.

According to various example embodiments, in order to enhance measurement efficiency, configuration of the electronic device 300 may be considered in an accessory form hanging at a ceiling such as a mobile.

Figure 4:
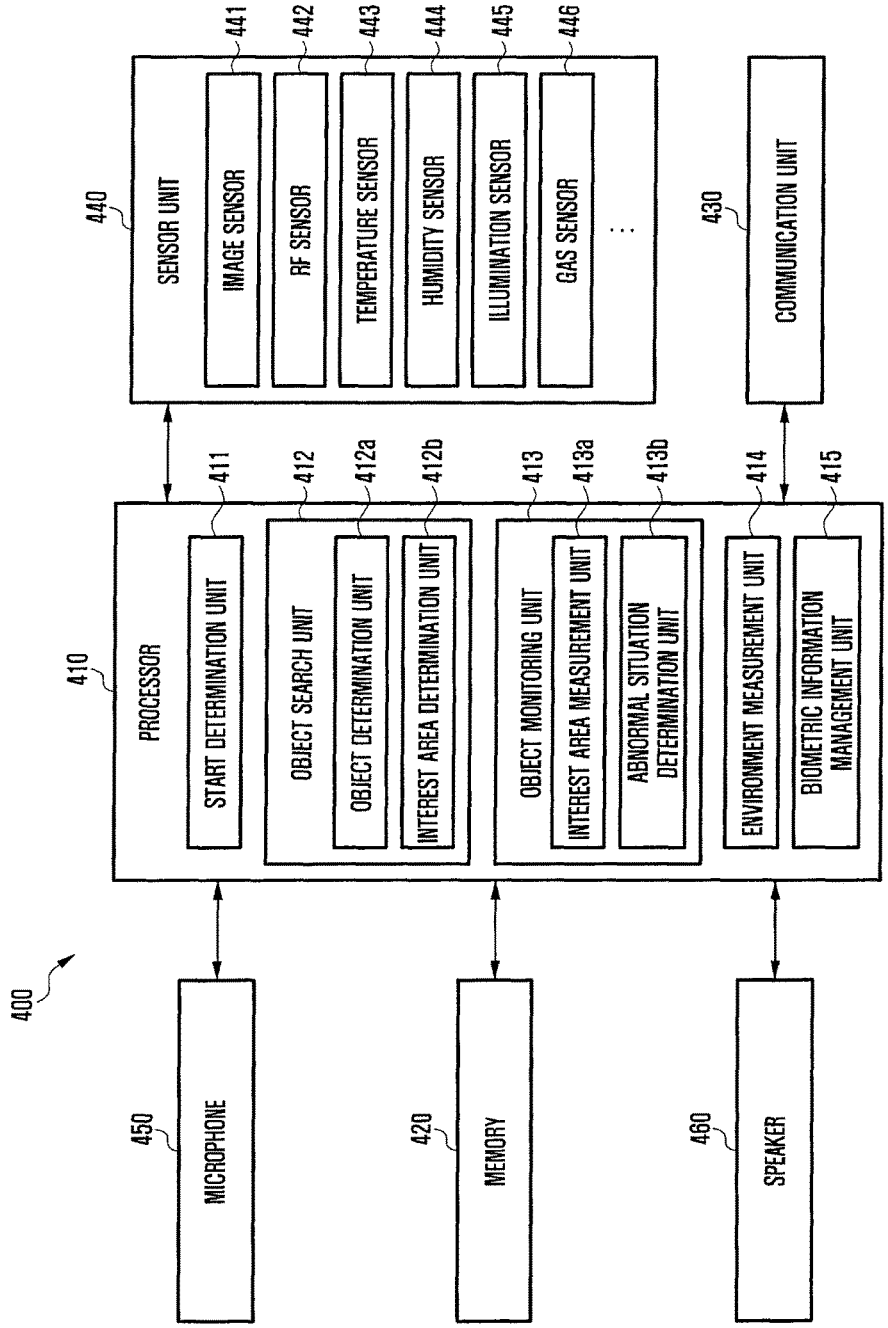
FIG. 4 is a block diagram illustrating a configuration of an electronic device according to an example embodiment of the present disclosure.

FIG. 4 is a block diagram illustrating a configuration of an electronic device 400 according to an example embodiment of the present disclosure.

An electronic device 400 of FIG. 4 may include a processor 410, memory 420, communication unit 430, sensor unit 440, microphone 450, and speaker 460. FIG. 4 illustrates various constituent elements that the electronic device 400 may have according to various example embodiments, but the electronic device 400 may be implemented into a configuration that excludes some of the constituent elements. For example, the electronic device 400 may be configured with a processor 410, memory 420, image sensor 441, and RF sensor 442. In another example, when the electronic device 400 communicates with an external device (not shown), the electronic device 400 may be configured with the processor 410, the memory 420, the image sensor 441, the RF sensor 442 and the communication unit 430.

The processor 410 may include a plurality of function units that may determine a state of objects.

As shown in FIG. 4, the processor 410 may include an object search unit 412, object monitoring unit 413, environment measurement unit 414, and biometric information management unit 415. In this case, the processor 410 may include some of the foregoing constituent elements. For example, the processor 410 may include an object search unit 412 and an object monitoring unit 413. The foregoing function units may be implemented using at least one of a software program, hardware circuit, and semiconductor chip.

A start determination unit (or a hypnagogic stage determination unit) 411 of the processor 410 may determine whether to start monitoring of an object. For example, the start determination unit 411 may determine whether to start monitoring of a user sleep state according to whether the user is in a hypnagogic stage.

For example, the start determination unit 411 may determine whether the user is in a hypnagogic stage based on a sensing value detected using the image sensor 441 or the RF sensor 442. Alternatively, the start determination unit 411 may determine whether a user is in a hypnagogic stage based on information received from a wearable device that the user wears. Alternatively, the start determination unit 411 may determine whether the user is in a hypnagogic stage based on information received from an Internet of things (IoT) device around the user.

If the user is in a hypnagogic stage, the start determination unit 411 may request monitoring of a user sleep state. For example, the start determination unit 411 may transmit a triggering signal that requests to the object search unit 412 to start monitoring of a sleep state.

In another example, when an input signal that requests a start to monitoring of an object is received, the start determination unit 411 may transmit a triggering signal that requests the start of monitoring. An input signal that requests the start of monitoring may be a signal generated according to a user input that selects a user interface (UI) provided in the electronic device 400 or may be a signal received from an external device according to a user input through an external device (not shown) connected to the electronic device 400 by communication means.

The object search unit 412 may determine at least one object triggering monitoring. For example, the object search unit 412 may determine at least one user in which monitoring of a sleep state is to be executed.

The object search unit 412 may include an object determination unit 412a and an interest area determination unit 412b.

The object determination unit 412a may apply a face recognition or person recognition algorithm to image information photographed by an image sensor. When a plurality of objects are recognized as an algorithm application result, the object determination unit 412a may determine the plurality of recognized objects to be a monitoring candidate object.

The object determination unit 412a may notify a user of the number of determined monitoring candidate objects. For example, when the object determination unit 412a transmits the number of the objects to the external device (not shown) through the communication unit 430, the external device may provide the number of objects to the user.

Alternatively, the object determination unit 412a may transmit image information about each of monitoring candidate objects to the external device through the communication unit 430. The external device may provide received image information to the user.

When the user determines the number of objects to monitor or selects an object to monitor with reference to the number or image information about the object, the object determination unit 412a may determine a monitoring candidate object that receives a determination of the user or a selected monitoring candidate object to be a monitoring target object to be searched for an interest area.

In another example, the object determination unit 412a may determine a monitoring target object using already recognized history information. For example, when at least a portion of monitoring candidate objects is an object already determined by the user or selected by the user, the object determination unit 412a may automatically determine the object to be a monitoring target object.

In another example, the object determination unit 412a may determine an entire object found within a predetermined area to be a monitoring target object.

When at least one object on which to perform monitoring is determined by the object determination unit 412a, the interest area determination unit 412b may determine an interest area of the at least one object.

Alternatively, when a plurality of objects on which to perform monitoring is determined, the interest area determination unit 412b may sequentially or randomly determine each of a first interest area of a first object and a second interest area of a second object among the plurality of objects.

For example, when the object is a person, the interest area may be at least a portion of a face, chest, head, abdomen, shoulder, or leg of a person. Alternatively, the interest area may be a nose, mouth, or neck of a person.

The interest area determination unit 412b may determine an interest area based on at least one of a user sleep posture, skin exposure area, clothing wearing state, body portion, and designated interest area history.

When a plurality of monitoring target objects exist, the interest area determination unit 412b may determine each object to be an interest area. For example, the interest area determination unit 412b may determine different body portions of each of a plurality of users to be an interest area.

Figure 5:
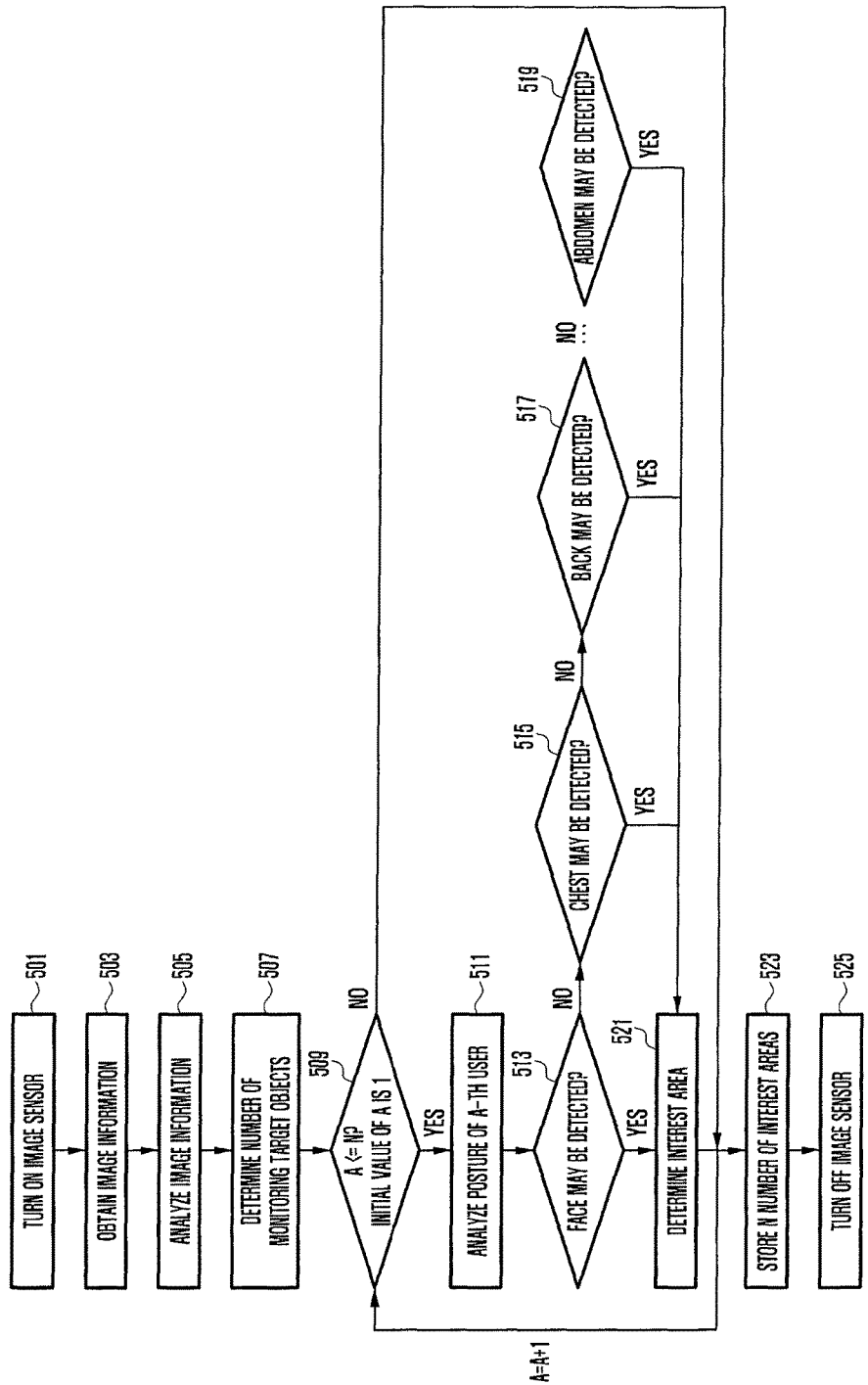
FIG. 5 is a flowchart illustrating a process in which an object search unit determines an interest area according to an example embodiment of the present disclosure.

FIG. 5 is a flowchart illustrating a process in which an object search unit 412 determines an interest area according to an example embodiment of the present disclosure With reference to FIG. 5, a state of an image sensor may be converted to an activated or "on" state at operation 501.

The object search unit 412 may obtain image information using an image sensor at operation 503.

The object search unit 412 may analyze the obtained image information at operation 505.

The object search unit 412 may determine the number of monitoring target objects as a result of the analysis at operation 507 (e.g., a number of users).

The object search unit 412 may determine and store an interest area for each respective monitoring target object through operations 509 to 523.

First, the object search unit 412 may set an initial value of a variable "A" to "1" at operation 509 and determine whether a value of the variable A (i.e., the number of objects determined at operation 507) is N or less.

If a value of the variable A is N or less, the object search unit 412 may analyze a posture of an A-th user at operation 511. That is, the object search unit 412 may sequentially review a user body portion that can sense a user biological signal (e.g., heartbeat related signal or breath related signal).

For example, the object search unit 412 may determine whether a face is detectable at operation 513. Specifically, the object search unit 412 may determine whether a face is exposed.

If a face cannot be detected, the object search unit 412 may determine whether a chest is detectable at operation 515.

If a chest cannot be detected, the object search unit 412 may determine whether a back is detectable at operation 517.

If a back cannot be detected, the object search unit 412 may determine whether an abdomen is detectable at operation 519.

It is noted that an order of detection for the various body portions seen in operations 513 to 519 is provided here as a mere example and may be changed to a different order.

For example, a detection order may be preset to a default order, may be changed by a user, or may be determined based on an existing detection history. As an example of determining based on an existing detect history, an area that may be easily detected with less noise among conventionally measured interest areas may have a high priority. Various body portions such as a hand or a foot in addition to the foregoing body portions may be determined to be an interest area target.

The object search unit 412 may determine at least one body portion that can be detected among body portions of an A-th user to an interest area at operation 521 according to a determination result of operations 513 to 519.

Thereafter, the object search unit 412 may increase a value A and determine an interest area for each of the N number of users by repeating the value A not to exceed the object number N.

When the "N" number of interest areas are determined for each of the N number of users, the object search unit 412 may store the determined N number of interest areas at operation 523.

A plurality of interest areas may be determined for one user; and, in this case, the object search unit 412 may store a N or more number of interest areas.

When an interest area is determined, a state of the image sensor may be again converted to a deactivated or "off" state at operation 525.

According to various example embodiments, when a triggering signal is received in the start determination unit 411, the object search unit 412 may be executed or may be automatically executed at every predetermined period.

Further, the object search unit 412 may store image information of at least one of the foregoing monitoring candidate object, monitoring target object, and interest area. In this case, in order to enable a user to make a determination, the electronic device 400 may transmit the image information to an external device (not shown).

When an interest area of an object is determined in the object search unit 412, the object monitoring unit 413 of the processor 410 may monitor the interest area to obtain biometric information about the object.

The object monitoring unit 413 may include an interest area measurement unit 413a that obtains biometric information, and an abnormal situation determination unit 413b that is capable of detecting an abnormal situation of an object.

The interest area measurement unit 413a may transmit an RF signal to an interest area and obtain user biometric information based on a reflected RF signal.

Specifically, the interest area measurement unit 413a may transmit an RF signal to a body portion and obtain movement information according to a change of a body portion based on a reflected RF signal. The interest area measurement unit 413a may obtain information about a user sleep state based on the obtained movement information. In this case, the interest area measurement unit 413a may additionally perform a process of removing noise of a movement of a body portion.

When a plurality of monitoring target objects exist, the interest area measurement unit 413a may obtain first biometric information based on an RF signal reflected from a first interest area of a first object and obtain second biometric information based on an RF signal reflected from a second interest area of a second object.

Further, when a plurality of interest areas are determined for one object, the interest area measurement unit 413a may obtain first biometric information based on an RF signal reflected from a first interest area of the object and obtain second biometric information based on an RF signal reflected from a second interest area of the object.

Figure 6:
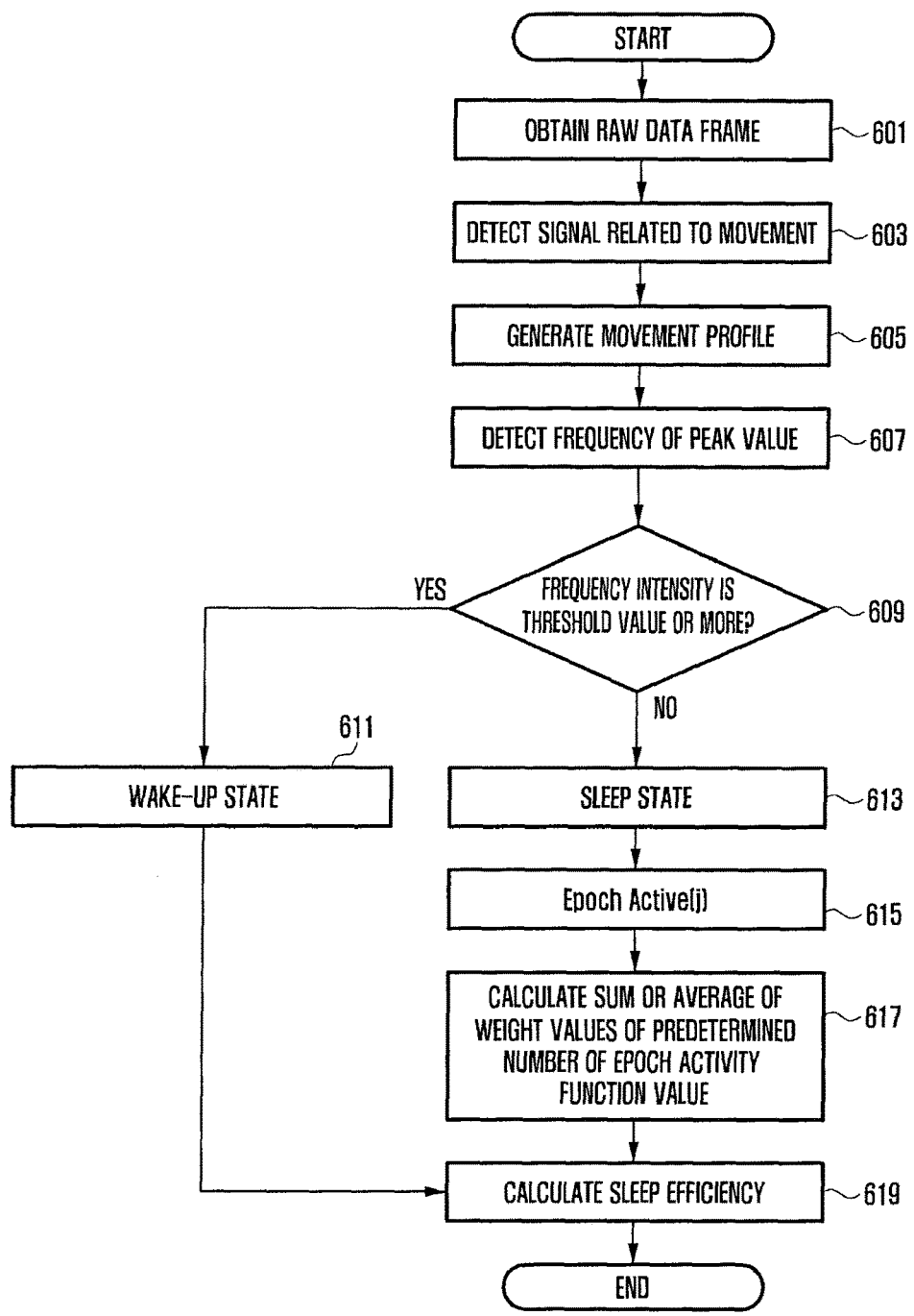
FIG. 6 is a flowchart illustrating a process in which an object monitoring unit obtains biometric information about an object according to an example embodiment of the present disclosure.

FIG. 6 is a flowchart illustrating a process in which an object monitoring unit 413 obtains biometric information about an object according to an example embodiment of the present disclosure.

The object monitoring unit 413 may obtain a "Doppler" raw data frame with an RF signal reflected in an interest area using the RF sensor at operation 601.

The object monitoring unit 413 may detect a signal related to a movement of the interest area from among a number of reflected RF signals at operation 603.

The object monitoring unit 413 may generate a movement profile using a signal related to the detected movement at operation 605. That is, the electronic device may obtain a movement profile generated based on detected movement information.

The object monitoring unit 413 may detect a peak value frequency in the movement profile at operation 607.

The object monitoring unit 413 may determine whether detected frequency intensity is equal to or greater than a threshold value at operation 609.

If detected frequency intensity is equal to or greater than the threshold value, the object monitoring unit 413 may determine at operation 611 that a user is has awoken (e.g., is in a "waking" or "wake-up" state). That is, the object monitoring unit 413 may obtain biometric information indicating the user's wake-up state.

If a user is in the wake-up state, the object monitoring unit 413 may calculate user sleep efficiency at operation 619. In this case, the object monitoring unit 413 may analyze one or more user sleep stages and calculate user sleep efficiency based on the user sleep stage.

In contrast, if detected frequency intensity is less than a threshold value, the object monitoring unit 413 may determine that the user remains in asleep (e.g., in a sleep state) at operation 613. That is, the object monitoring unit 413 may obtain biometric information indicating a sleep state for the user.

If the user is in the sleep state, the object monitoring unit 413 may detect a user biological signal at operation 615 using an "epoch" activity function, which is a user biological activity measurement function. The user biological signal may include, for example, at least one of user heartbeat, breath, body temperature, blood pressure, or movement signal.

The object monitoring unit 413 may calculate the sum or an average of weight values of the predetermined number (e.g., 5 to 10) of an epoch activity function value at operation 617.

The object monitoring unit 413 may calculate user sleep efficiency based on a calculated result at operation 619.

While measuring a plurality of objects in the interest area measurement unit 413a, the abnormal situation determination unit 413b may determine an abnormal situation of a specific object.

For example, the abnormal situation determination unit 413b may determine whether the user is in an abnormal sleep state, such as sleep apnea.

If the user is in an abnormal sleep state, the interest area measurement unit 413a may target an object corresponding to the abnormal situation to intensify measurement of a specific object for a designated time.

For example, after the user starts to experience apnea, which is determined to be an abnormal situation, then until the apnea is terminated, the interest area measurement unit 413a may intensify collection of biometric information about the user. In particular, when a plurality of interest areas of the user are determined, the interest area measurement unit 413a may obtain biometric information about the user while alternately detecting the plurality of interest areas.

In another example, the abnormal situation determination unit 413b may determine a situation in which a biological signal is not measured in an interest area. The situation in which a biological signal is not measured may be, for example, a situation in which a user separates from a bed in sleep by somnambulism, a situation in which a user tosses and turns or sleeps in a sit-down state, and a situation in which a user wakes up temporarily and goes to a toilet during a sleep stage.

In this case, the object monitoring unit 413 may transmit a signal that requests re-search of a monitoring target object to the object search unit 412.

The object search unit 412, having received the re-request signal may re-search for an object to monitor using, for example, an image sensor.

The environment measurement unit 414 may obtain environment information about an object. For example, the environment measurement unit 414 may obtain environment information related to a sleep environment of a user in sleep.

In order for the user to determine environment information, the electronic device 400 may transmit measured environment information to an external device (not shown) of the user. Further, in order to enhance a user sleep quality, the electronic device 400 or the external device may together provide various items of guide information that can guide a sleep environment.

The biometric information management unit 415 may manage image information photographed by a photographing sensor, a sensing value measured by the sensor, or biometric information about an object obtained based on the sensing value. For example, the biometric information management unit 415 may manage, for example, image information of a user in sleep, an RF signal value of a user interest area, movement information about an interest area obtained based on the RF signal, or biometric information obtained based on the movement information.

In various example embodiments, the biometric information management unit 415 may store at least a portion of the information at a security area of the memory 420. The security area of the memory 420 may be, for example, an Embedded Secure Element (eSE) area or a trust zone (e.g., an area that may be accessed through a Samsung KNOX mode).

In this case, the biometric information management unit 415 may apply a security level to the information to manage the information.

For example, information of a first level is information of a low security level and may be raw data in relation to user privacy.

Further, information of a second level is information of a high security level and may be data processed by a filtering processing, security setup, or a mosaic processing.

When the electronic device 400 transmits user monitoring information to an external device, the electronic device 400 may change information of a first level to information of a second level of a high security level. The electronic device 400 may transmit the information of a changed second level to an external device (not shown).

According to various example embodiments, the biometric information management unit 415 may classify and manage the information on a sleep stage basis. In this case, the biometric information management unit 415 may compress and store information about a normal sleep stage and separately analyze and store data of an abnormal sleep stage.

The sensor unit 440 may further include an image sensor 441, RF sensor 442, temperature sensor 443, humidity sensor 444, illumination sensor 445, and gas sensor 446.

The electronic device 400 may obtain biometric information about an object based on information detected by the foregoing various kinds of sensors or may obtain object peripheral environment information.

Further, the electronic device 400 may enhance user sleep environment based on information detected by the foregoing various kinds of sensors. The electronic device 400 may provide, for example, an air purification function, humidification function, lighting function, sound providing function, or oxygen supply function based on detected information to provide an optimal sleep environment to the user.

The communication unit 430 may transmit user state information or environment information to the external device (e.g., user terminal device). In this case, the communication unit 430 may transmit the data to the external device using near field communication (NFC), third-generation (3G), radio frequency identification (RFID), and human body communication (HBC) technology. A detailed example of the communication unit 430 will be described in detail later using a communication module 2220 of FIG. 22.

The microphone 450 may measure a sound (e.g., snoring nose of a user in sleep) that generates an object or a sound of an environment in which an object is located. For accurate measurement of a location and a magnitude of a sound, the microphone 450 may be configured in an array form including a plurality of microphones.

The speaker 460 may output a sound and provide various services based on image information or biometric information about an object obtained by the electronic device 400. For example, the speaker 460 may provide music or an alarm before a user wakes up or at a time point at which a user wakes up or may provide music, news, or radio after a user falls asleep. Alternatively, when a message or a phone call to a user is received by a smart phone or wearable device, the electronic device 400 may receive the message or phone call by receiving information through a short range network to output the message or the phone call of the receiving information with a sound through the speaker 460.

Figure 7:
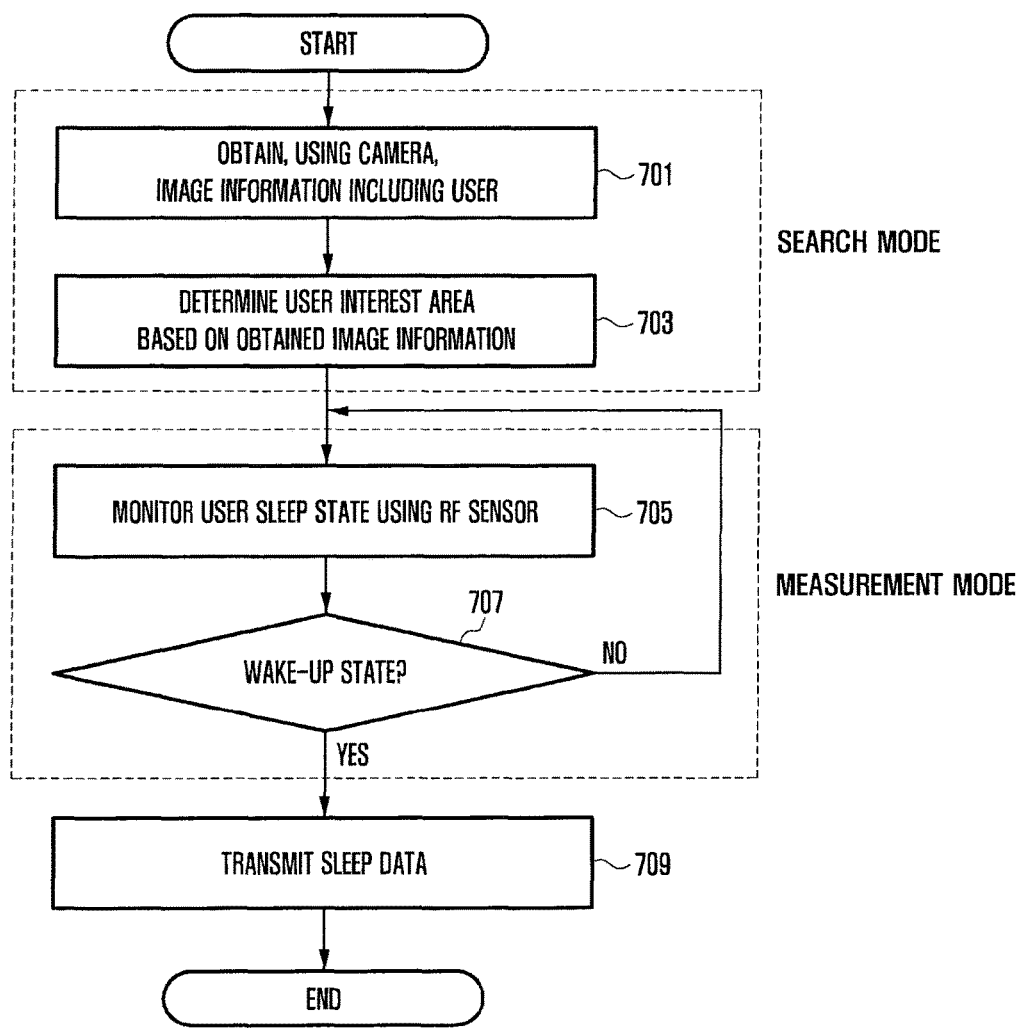
FIG. 7 and FIG. 8 are flowcharts illustrating a process in which an electronic device transmits sleep data according to an example embodiment of the present disclosure.
Figure 8:
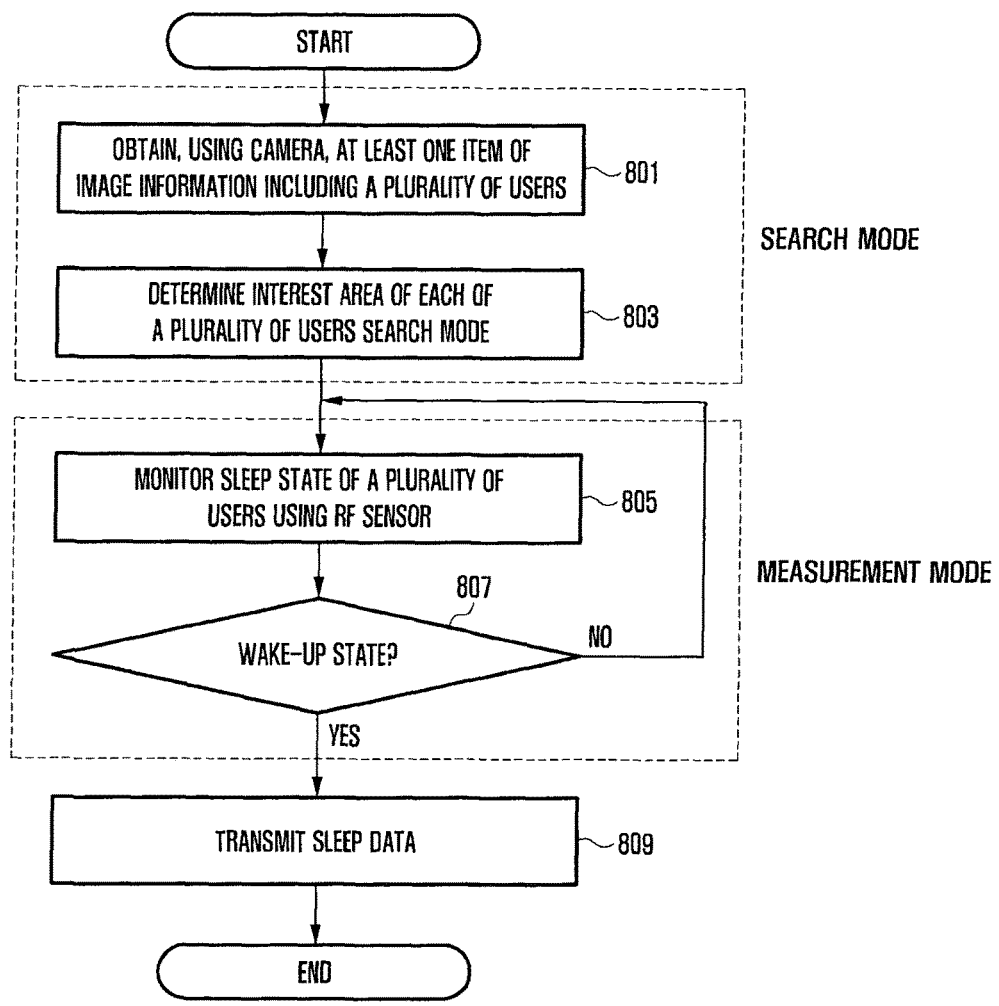

According to various example embodiments, the electronic device may transmit user sleep data to a user terminal through a process of FIGS. 7 and 8.

FIG. 7 is a flowchart illustrating a process in which an electronic device transmits sleep data according to an example embodiment of the present disclosure.

At operation 701, the electronic device may, using a camera, obtain image information including a user.

Thereafter, the electronic device may determine a user interest area based on the obtained image information at operation 703.

In this case, operations 701 and 703 may be included in a process in which the electronic device operates in a search mode.

When an interest area of an object is determined, the electronic device may monitor a user sleep state using the RF sensor at operation 705.

For example, the electronic device may detect an RF signal reflected in a designated interest area using the RF sensor and obtain sleep state information as user biometric information based on the detected RF signal.

Thereafter, the electronic device may determine whether a user sleep state is a wake-up state at operation 707.

In this case, operations 705 and 707 may be included in a process in which the electronic device operates in a measurement mode.

If the user is not in a wake-up state, the electronic device may continue to monitor a user sleep state using the RF sensor.

If the user is in a wake-up state, the electronic device may transmit user sleep data to an external device (not shown) at operation 709. Alternatively, the electronic device may store sleep data. The sleep data may include at least one of, for example, image information of a user in sleep, a sensing value of a user interest area, movement information obtained based on the sensing value, and user sleep state information obtained based on the movement information.

FIG. 8 is a flowchart illustrating a process in which an electronic device transmits sleep data according to an example embodiment of the present disclosure.

At operation 801, the electronic device may obtain, using a camera, at least one item of image information including a plurality of users.

Thereafter, the electronic device may determine an interest area of each of a plurality of users based on at least one obtained item of image information at operation 803.

In this case, operations 801 and 803 may be included in a process in which the electronic device operates in a search mode.

In this case, the electronic device may distinguish each of the plurality of users. The electronic device may distinguish between the plurality of users based on image information, such as, for example, facial features, color, body size, clothing color, or movement habits of each of the plurality of users. Alternatively, the electronic device may distinguish each of a plurality of users based on biometric information of each of the users (e.g., heart rate, breath number, or body temperature) detected by a terminal or a wearable device of a plurality of users.

Further, interest areas may be determined to different portions of each of a plurality of users. For example, when an interest portion of a first user of a plurality of users is a chest, an interest portion of a second user may be determined to be an abdomen.

Thereafter, the electronic device may monitor sequentially, randomly, or according to a predetermined rule a sleep state of a plurality of users using the RF sensor at operation 805.

For example, the electronic device may transmit sequentially, randomly, or according to a predetermined rule an RF signal to a plurality of interest areas of a plurality of users using the RF sensor. The electronic device may obtain sleep state information as biometric information about each of a plurality of users based on an RF signal reflected from the plurality of interest areas that corresponds to the transmitted RF signal.

Thereafter, the electronic device may determine whether a state of at least one user of a plurality of users is a wake-up state at operation 807.

In this case, operations 805 and 807 may be included in a process in which the electronic device operates in a measurement mode.

If some users of a plurality of users are not in a wake-up state, the electronic device may continue to monitor a sleep state of some users using the RF sensor.

If some users of a plurality of users are in a wake-up state, the electronic device may transmit sleep data for the user in the wake-up state to an external device (not shown) at operation 809. In this case, the external device may be a device (e.g., a smart phone) of the user in a wake-up state. Alternatively, the electronic device may store sleep data of the user in a wake-up state. Further, the device may continue monitoring the sleep state of other users who did not awaken.

Figure 9:
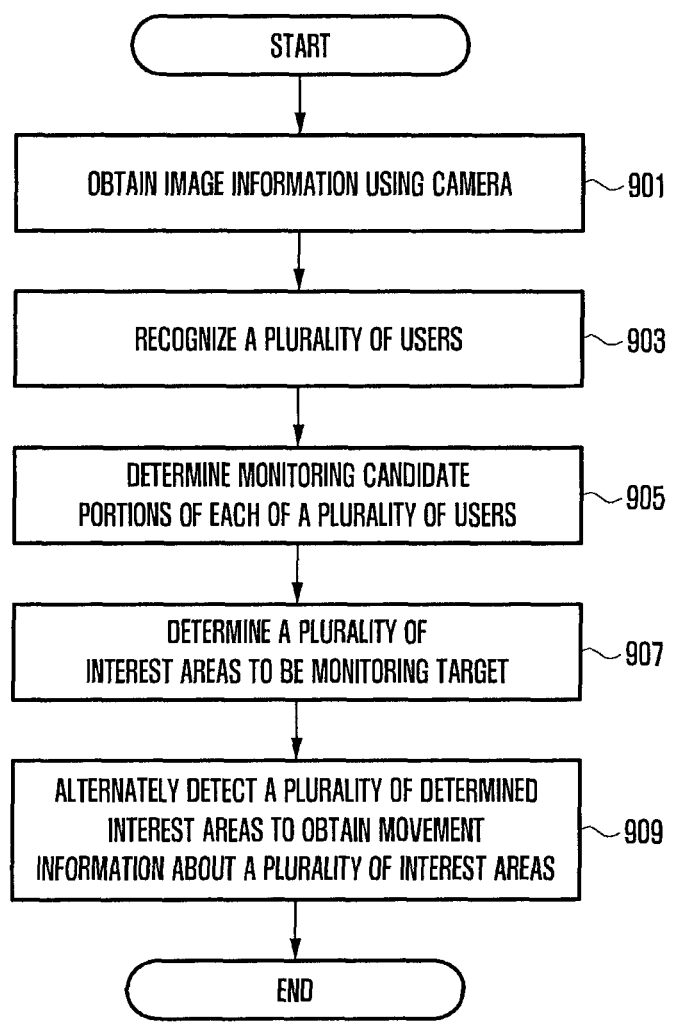
FIG. 9, FIG. 10 and FIG. 11 are flowcharts illustrating a process in which an electronic device obtains movement information according to an example embodiment of the present disclosure.
Figure 10:
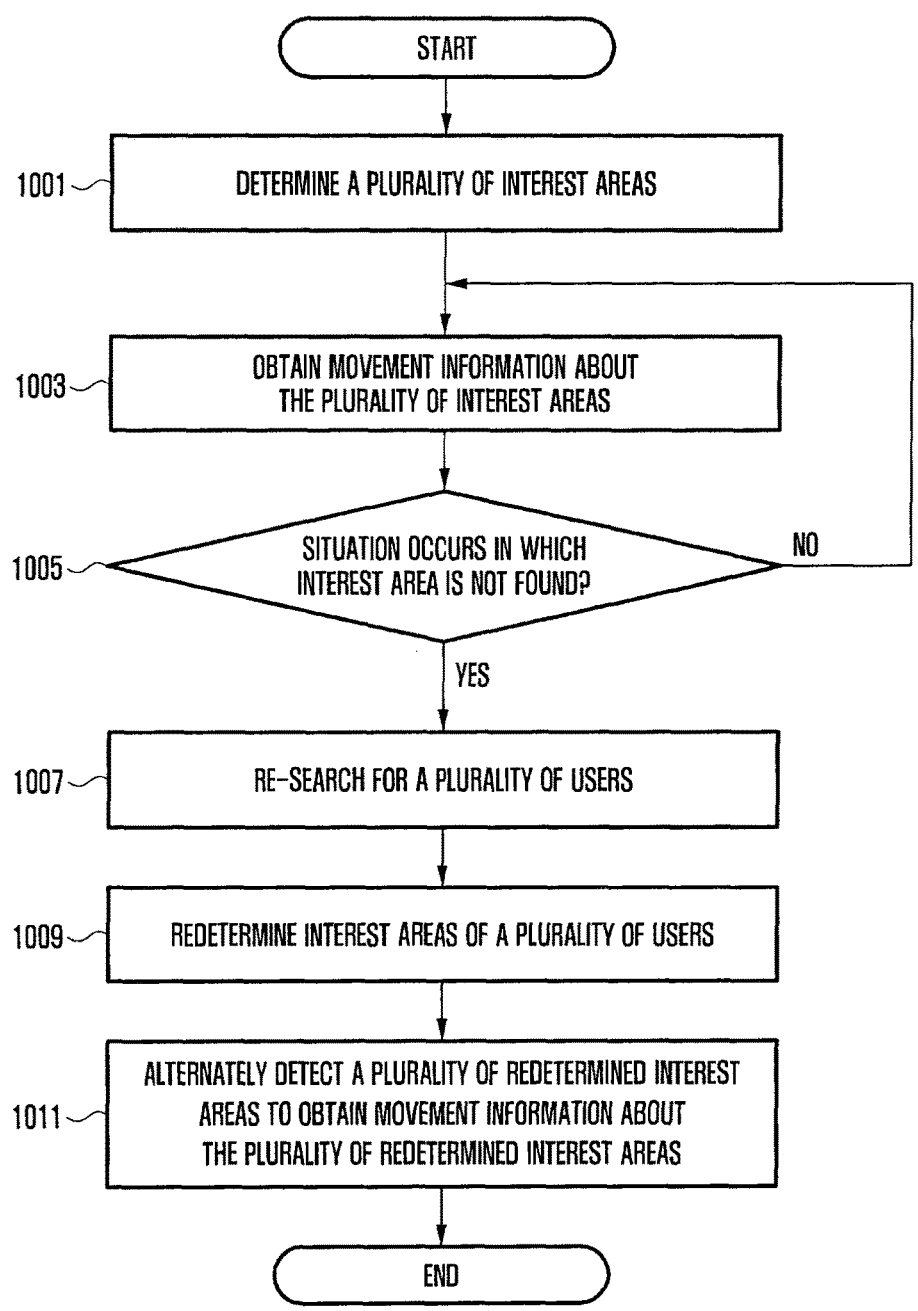
Figure 11:
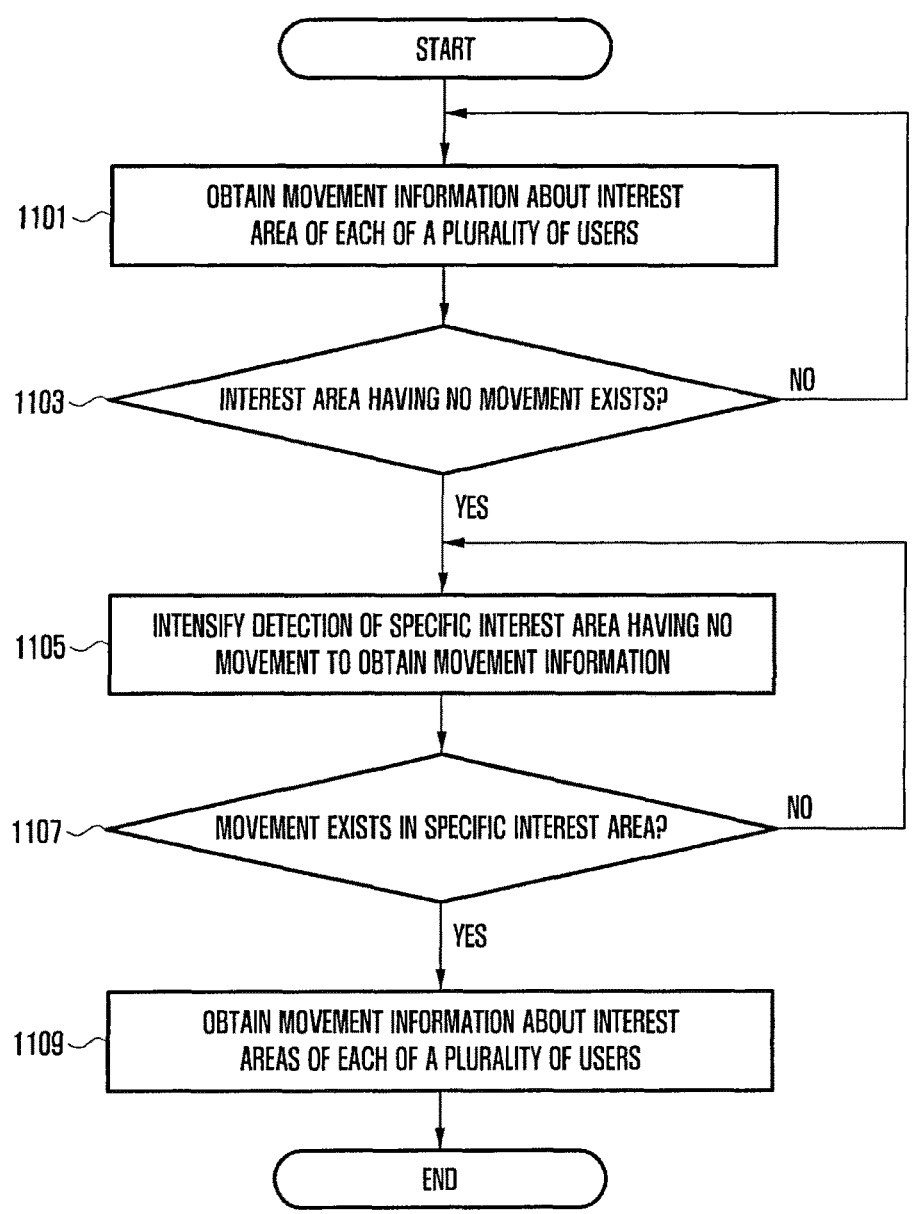

According to various example embodiments, the electronic device may obtain user movement information through a process of FIGS. 9 to 11.

FIG. 9 is a flowchart illustrating a process in which an electronic device obtains movement information according to an example embodiment of the present disclosure.

The electronic device may obtain image information using a camera at operation 901.

The electronic device may, at operation 903, recognize a plurality of users within a photographing range based on the obtained image information.

Thereafter, the electronic device may determine monitoring candidate portions of each of a plurality of users at operation 905.

The candidate portion may be determined, for example, based on a body portion of each of a plurality of users. The body portion may be determined, for example, in order of a user chest, nose, mouth, and shoulder.

The electronic device may determine a plurality of interest areas to be a monitoring target among the determined monitoring candidate portions at operation 907.

The interest area may be determined in consideration of a predefined threshold value in a candidate portion. For example, when there is noise of a threshold value or more in some of candidate portions, the candidate portion may be excluded from an interest area target. For example, when a candidate portion is exposed to a threshold value or less according to a user sleep posture and a clothing wearing state, the candidate portion may be excluded from an interest area target.

When a plurality of interest areas are determined, the electronic device may, at operation 909, alternately detect a plurality of determined interest areas to obtain movement information about the plurality of interest areas.

For example, the electronic device may transmit an RF signal to a plurality of interest areas and obtain movement information about the plurality of interest areas based on the reflected RF signal.

The electronic device may store obtained movement information about the plurality of interest areas or may transmit obtained movement information about the plurality of interest areas to an external device.

FIG. 10 is a flowchart illustrating a process in which an electronic device obtains movement information in a situation where a user is not found according to another example embodiment of the present disclosure.

The electronic device may determine a plurality of interest areas of each of a plurality of users at operation 1001.

In detecting the plurality of determined interest areas, the electronic device may obtain movement information about the plurality of interest areas at operation 1003.

In this case, in order to avoid superfluous repeated descriptions of the invention, a detailed description of a process of operations 1001 and 1003 will be omitted as they correspond to that of operations 901 to 909 of FIG. 9.

In this case, the electronic device may determine whether a situation occurs in which at least one interest area of a plurality of interest areas is not detected in operation 1005.

If the situation occurs in which at least one interest area of the plurality of interest areas is not detected, the electronic device may re-search for a plurality of users at operation 1007.

The electronic device may re-determine interest areas of a plurality of re-found users at operation 1009.

The electronic device may, at operation 1011, alternately detect a plurality of re-determined interest areas to obtain movement information about the plurality of re-determined interest areas.

The electronic device may store movement information about the plurality of obtained interest areas or may transmit movement information about the plurality of obtained interest areas to an external device.

FIG. 11 is a flowchart illustrating a process in which an electronic device detects movement information for a user apnea situation according to another example embodiment of the present disclosure.

The electronic device may obtain movement information about an interest area for each user of a plurality of users at operation 1101.

A process in which the electronic device obtains movement information has been described at operations 901 to 909 of FIG. 9; therefore, a detailed description thereof will be omitted.

Thereafter, the electronic device may determine, at operation 1103, whether a specific interest area having no movement exists among the plurality of interest areas based on obtained movement information.

If a specific interest area having no movement exists, the electronic device may intensify detection of the specific interest area to obtain movement information at operation 1105.

The electronic device may determine at operation 1107 whether a movement exists in a specific interest area based on movement information obtained at the specific interest area using the intensified detection.

If a movement exists in a specific interest area with termination of a user apnea situation, the electronic device may obtain again movement information about interest areas of each of a plurality of users at operation 1109.

Figure 12:
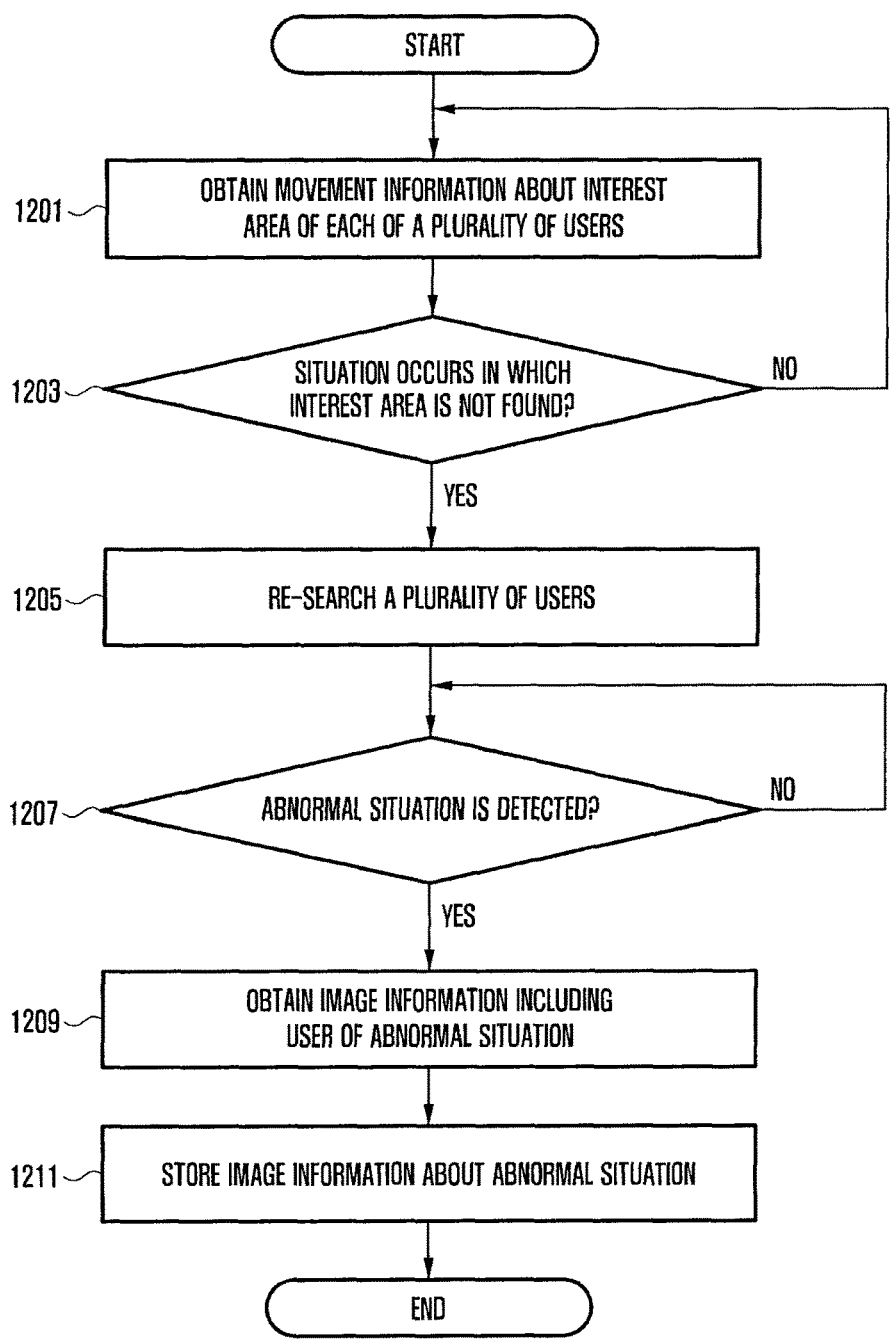
FIG. 12 is a flowchart illustrating a process of storing image information about an abnormal situation according to an example embodiment of the present disclosure.

According to various example embodiments, the electronic device may store image information about a user abnormal situation through a process of FIG. 12.

FIG. 12 is a flowchart illustrating a process of storing image information about an abnormal situation according to an example embodiment of the present disclosure.

The electronic device may obtain movement information about a plurality of interest areas of a plurality of users at operation 1201.

Thereafter, the electronic device may determine at operation 1203 whether a situation occurs in which at least one of interest areas of a plurality of interest areas is not found or detected.

If a situation occurs in which at least one of interest area of a plurality of interest areas is not found, the electronic device may re-search a plurality of users at operation 1205.

In this case, in order to re-search a plurality of users, the electronic device may convert a state of a camera thereof to an activation state or an "on" state.

The electronic device may then determine whether an abnormal situation is detected in at least one user of a plurality of users at operation 1207.

The abnormal situation may include, for example, a situation in which the user has a fit, walks, sits down, or has a nightmare in their sleep. Alternatively, the abnormal situation may include a situation in which biometric information about an object is not detectable.

If an abnormal situation is detected, the electronic device may obtain image information including a user in the abnormal situation using an image sensor at operation 1209. That is, an image of the abnormal state of the user may be captured.

Thereafter, the electronic device may, at operation 1211, store obtained image information about an abnormal situation. Further, the electronic device may transmit image information about an abnormal situation to a terminal of a user or a user guardian. Accordingly, the user or the user guardian may access the image of the abnormal sleep state.

FIG. 13 is a diagram illustrating a use process of an electronic device that monitors a user sleep state according to an example embodiment of the present disclosure.

An electronic device 1300 may be located, for example, at a periphery of a bed in which a user sleeps. This may serve as an advantageous location for monitoring a sleep state of users.

For example, the electronic device 1300 may be located near the feet of a plurality of users 1 and 2, as shown in FIG. 13A; near the head of a plurality of users 1 and 2, as shown in FIG. 13B; and/or beside a plurality of users 1 and 2 as shown in FIG. 13C.

The electronic device 1300 may obtain image information including a plurality of users 1 and 2 using an image sensor.

The electronic device 1300 may recognize a plurality of users 1 and 2 from the obtained image information. For example, the electronic device 1300 may apply a facial recognition algorithm or person recognition algorithm to recognize each of the plurality of users 1 and 2.

When a plurality of users 1 and 2 are recognized, the electronic device 1300 may determine a number of interest areas 1301-1306 for the plurality of users 1 and 2. The interest areas 1301-1306 may correspond to different body portions of the users, detectable according to a location of the electronic device 1300 and/or a sleep posture of the plurality of users 1 and 2.

The electronic device 1300 sequentially may measure designated interest areas 1301-1306, and the electronic device 1300 may thus monitor a sleep state of the plurality of users 1 and 2. In this case, when a specific event occurs, the electronic device 1300 may monitor a sleep state of a specific user with greater intensity. For example, when a movement of one interest area of interest areas 1301-1306 is not detected, the electronic device 1300 may intensify monitoring of a user sleep state related to the particular interest area.

FIG. 14 is a diagram illustrating sleep information related to a user sleep state and sleep environment information about a sleep environment displayed on a screen according to an example embodiment of the present disclosure.

An electronic device 1400 and an external device (e.g., a user smart phone 1450) may communicate with each other. When a communication channel is established between the electronic device 1400 and the external device 1450, the electronic device 1400 may transmit user image information, a sensing value of a user interest area, movement information obtained based on the sensing value, or user biometric information obtained based on the movement information to the external device 1450. Alternatively, the electronic device 1400 may transmit at least one of temperature information, humidity information, illumination information, and gas information as environment information around a user to the external device 1450.

The external device 1450 may display at least one item of information received from the electronic device 1400 on the screen. Alternatively, the external device 1450 may display information (e.g., text information, image information, or sleep guide information) generated based on received information on the screen. If the user wakes up, the external device 1450 may automatically provide the screen or may provide the screen when the user requests.

Figures 14A, 14B:
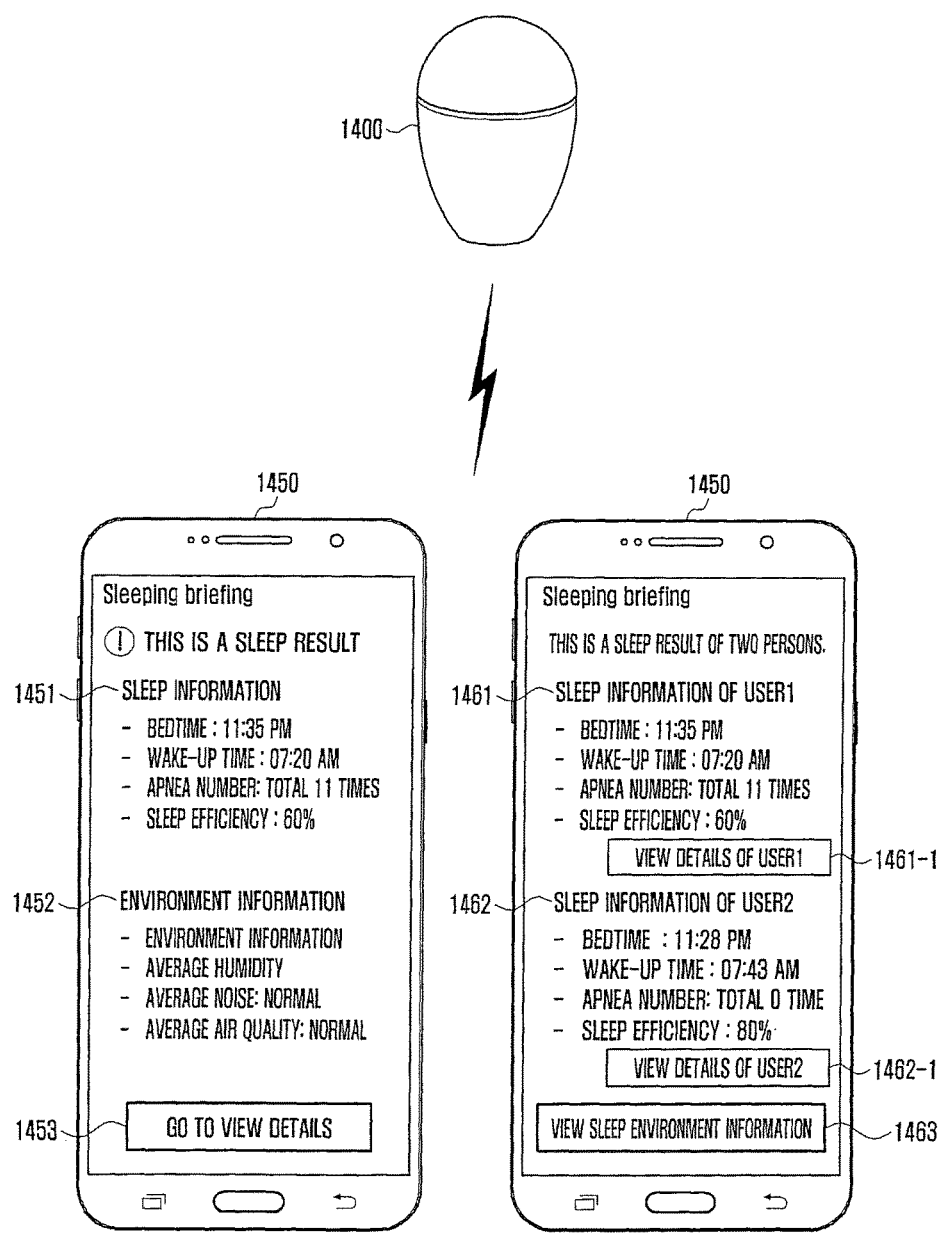
FIG. 14A and FIG. 14B are diagrams illustrating sleep information and sleep environment information displayed on a screen according to an example embodiment of the present disclosure.

FIG. 14A illustrates a screen of the external device 1450 that displays sleep information and environment information of one user.

On a screen of the external device 1450, sleep information 1451 may include at least one of a user hypnagogic stage start time (e.g., a bedtime), wake-up time, apnea number, and sleep efficiency. Sleep efficiency may be calculated, for example, based on a ratio of time spent in a deep sleep state (e.g., a rapid eye movement or "REM" sleep state) relative to an entirety of the user's sleep time.

Further, environment information 1452 may include, for example, at least one of an average temperature, average humidity, average noise, and an average air quality of a peripheral environment.

Further, a screen of the external device 1450 may further include a UI 1453 that can provide user detailed sleep information. In this case, when the UI 1453 is selected, a screen (e.g., screen of an external device, or element 1600 of FIG. 16A and FIG. 16B) including user detailed sleep information corresponding to the selected UI may be further displayed.

FIG. 14B illustrates a screen of the external device 1450 that displays sleep information for a plurality of users.

The screen of the external device 1450 may include, for example, sleep information 1461 of a first user and sleep information 1462 of a second user.

The sleep information 1461 of a first user may further include a first UI element 1461-1 selectable to provide detailed sleep information of the first user. Further, the sleep information 1462 of the second user may further include a second UI element 1462-1 selectable to provide second user detailed sleep information. In this case, when the first UI element 1461-1 or the second UI 1462-1 is selected, a screen (e.g., a screen of the external device 1600 of FIG. 16A and FIG. 16B) including user detailed sleep information corresponding to the selected UI element (and thus, the selected user) may be provided.

Further, a screen of the external device 1450 may further include a third UI element 1463 selectable to provide environment information. In this case, when the third UI element 1463 is selected, a screen including environment information in a user sleep state may be provided.

FIG. 15 is a diagram illustrating a screen for selecting a user to be provided with sleep information according to an example embodiment of the present disclosure.

Figures 15A, 15B:
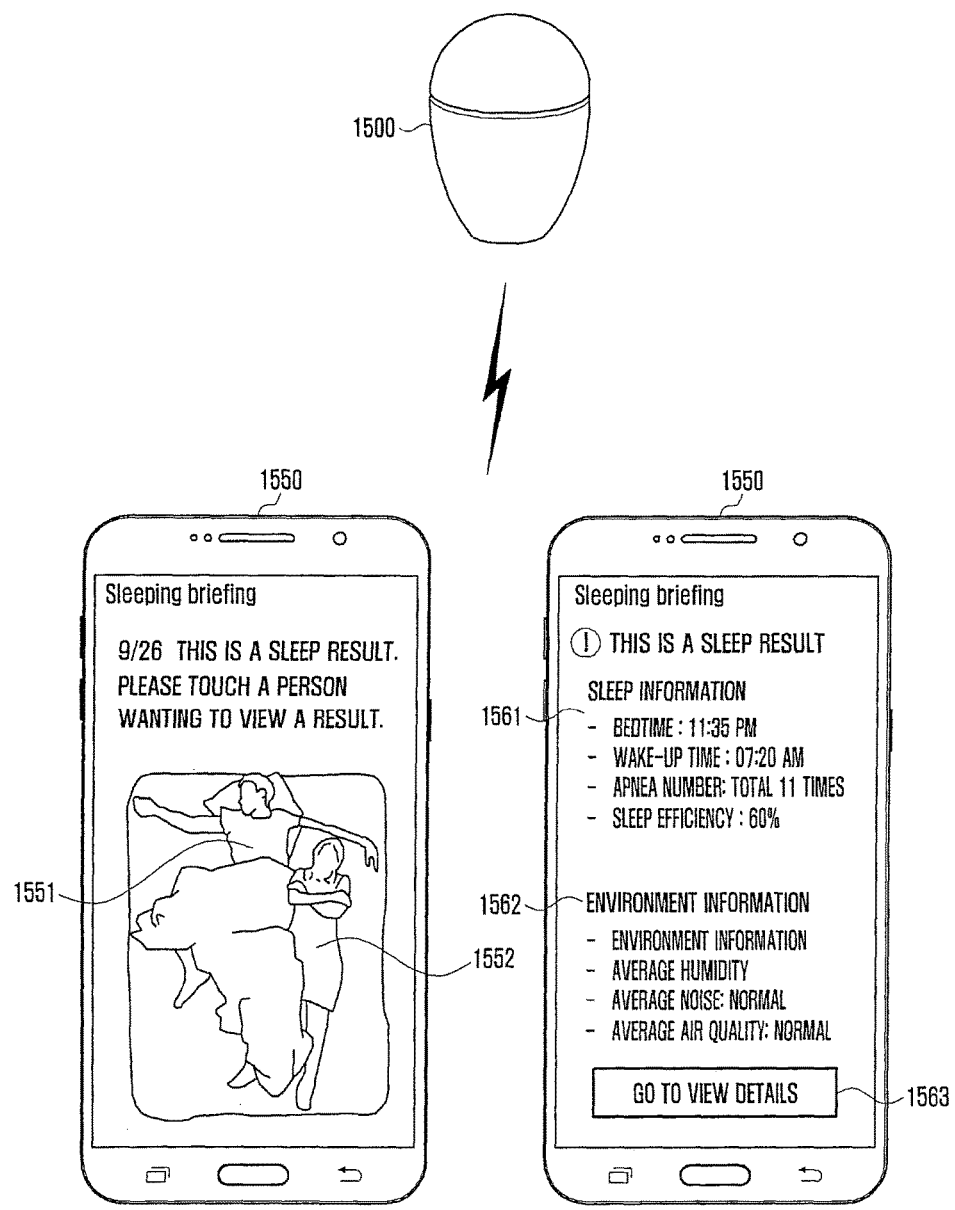
FIG. 15A and FIG. 15B are diagrams illustrating a screen for selecting a user to provide sleep information according to an example embodiment of the present disclosure.

As shown in FIG. 15A, an external device 1550 may receive image information photographed in the electronic device 1500 and display the received image information on a screen.

The image information may include an image of each of recognized users. When a plurality of images 1551 and 1552 each are mapped to a UI, the user may select one image of the plurality of images 1551 and 1552 displayed on the screen.

In this case, as shown in FIG. 15B, user sleep information 1561 and environment information 1562 corresponding to the selected image may be displayed on a screen of the external device 1550. Further, a screen of the external device 1550 may further include a UI element 1563 that can provide user detailed sleep information corresponding to a selected image when selected. In this case, when the UI element 1563 is selected, a screen (e.g., a screen of the external device 1600 of FIG. 16A and FIG. 16B) including user detailed sleep information corresponding to the selected UI may be further displayed.

According to various example embodiments, identification information (e.g., nickname or emoticon) instead of an image may be displayed on a screen. This may be replacement information used for protecting user privacy. In this case, when a user selects identification information, user sleep information and environment information corresponding to the selected identification information may be displayed on the screen.

FIG. 16 is a diagram illustrating a screen of an external device 1600 that displays detailed sleep information according to an example embodiment of the present disclosure.

Figures 16A, 16B:
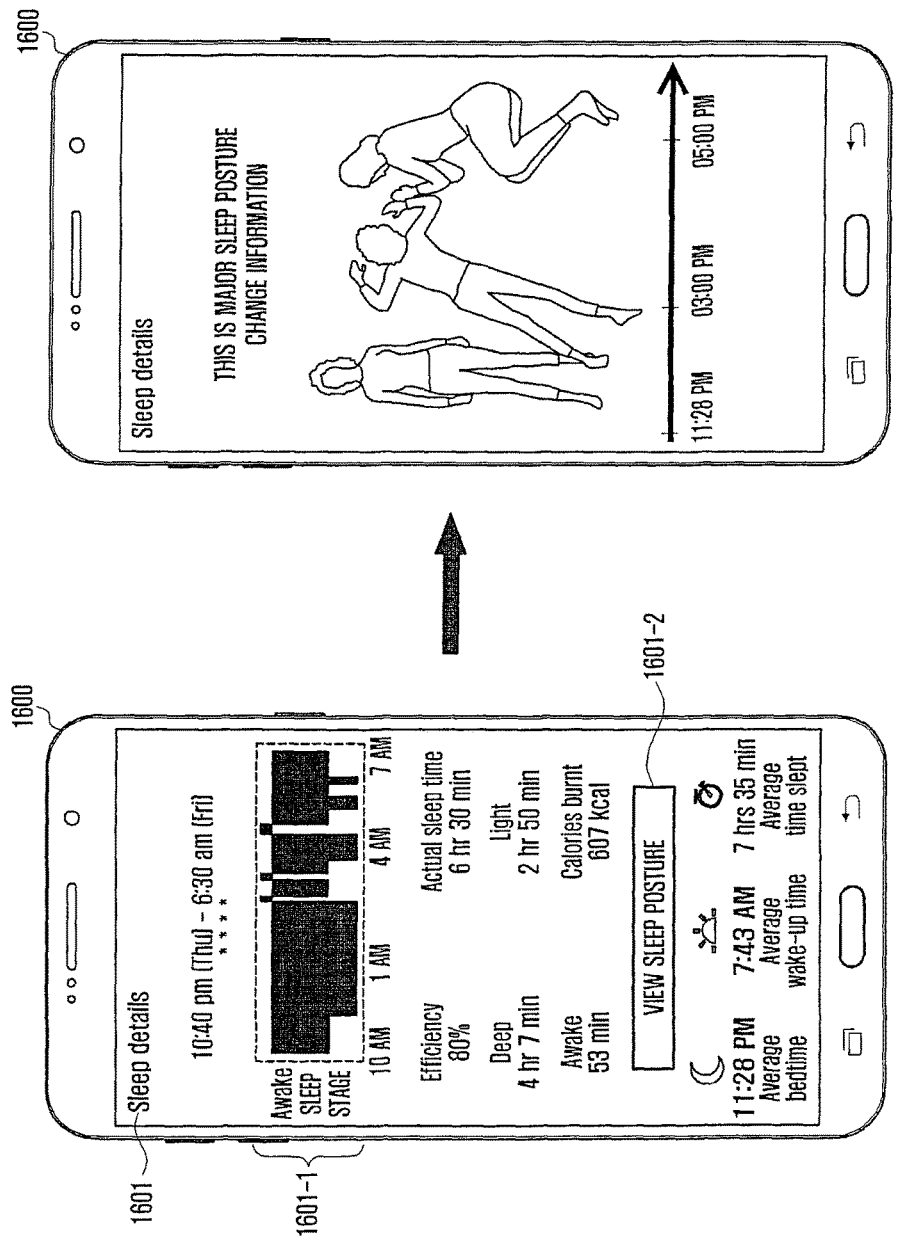
FIG. 16A and FIG. 16B are diagrams illustrating a screen of an external device that displays detailed sleep information according to an example embodiment of the present disclosure.

FIGS. 16A and 16B illustrate a screen that displays detailed sleep information 1601 of one user.

As shown in FIG. 16A, the detailed sleep information 1601 may include a graph 1601-1 representing progression of the user's sleep stages during sleep.

Further, the detailed sleep information may include at least one of sleep efficiency, a sleep time, a deep sleep time, a light sleep time, an awake time, calories consumed in sleep, an average hypnagogic stage state time (e.g., a bedtime of a user), an average wake-up time, and an average sleep time. In addition, a screen of the external device 1600 may display sleep environment information in a user sleep state. Further, the external device 1600 may display guide information that can enhance a user sleep state and sleep environment.

Further, detailed sleep information may include a UI element 1601-2 that is selectable to display user sleep posture.

When the UI element 1601-2 is selected, the external device 1600 may provide an image representing one or more sleep postures detected while the user slept, as shown in FIG. 16B.

For example, when a user's sleep posture is changed, the electronic device (not shown) may re-determine a user interest area. Whenever the electronic device re-determines an interest area, the electronic device may obtain image information including a user sleep posture using an image sensor. The electronic device may transmit to the external device 1600 image information including an obtained user sleep posture and time information when the image information was obtained.

Accordingly, as shown in FIG. 16B, the external device 1600 may display sequential images on a screen representing the changing sleep postures of the user. Alternatively, for privacy protection, the external device 1600 may display a replacement image instead of actual captures of the user on the screen.

In various example embodiments, in order to enhance user sleep efficiency, the external device 1600 may further display information that guides such that a user adopts a correct sleep posture based on user image information.

The electronic device may perform a function for enhancing a user sleep state or sleep environment based on a user sleep state.

Figure 17:
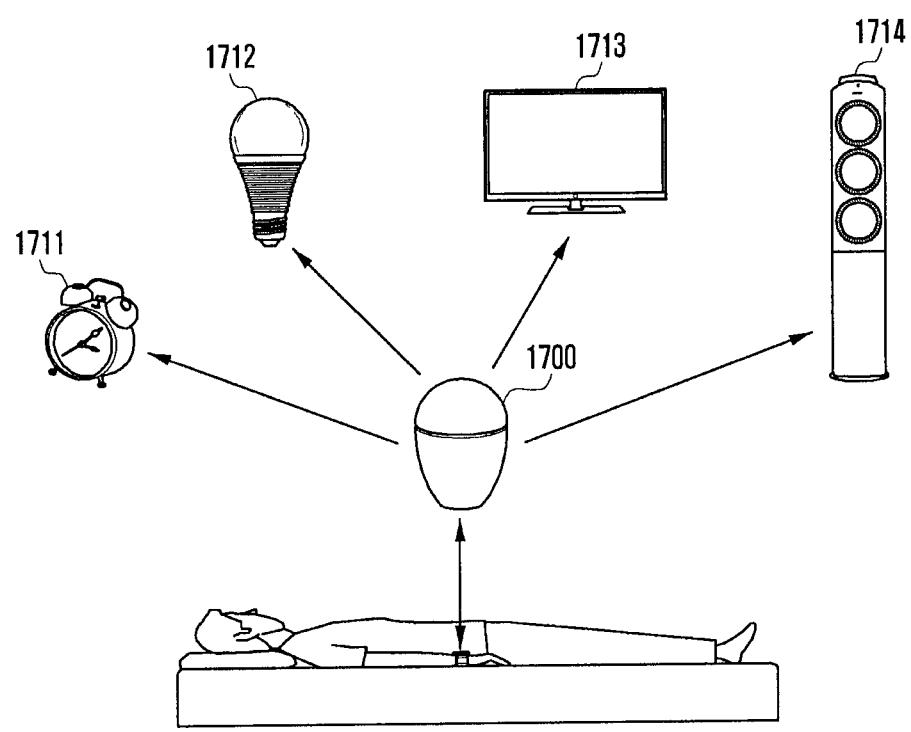
FIG. 17 is a diagram illustrating a use process of an electronic device in an Internet of things (IoT) environment according to an example embodiment of the present disclosure.

FIG. 17 is a diagram illustrating a use process of an electronic device in an Internet of things (IoT) environment according to an example embodiment of the present disclosure.

As shown in FIG. 17, an electronic device 1700 may perform a hub function to control IoT devices 1711-1714.

For example, the electronic device 1700 may control peripheral IoT devices 1711, 1712, 1713, and 1714 based on a user sleep state to enhance a user sleep state or sleep environment.

An electronic device according to the present disclosure may be used at various locations. For example, the electronic device may be used at a medical facility, a sanitarium, a day care center, a baby room, and a house of an elderly person who lives alone. In this case, peripheral IoT devices 1711-1714 controlled by the electronic device 1700 may be different according to a usage environment of the electronic device 1700. For example, when the user is located in a hospital room, the electronic device 1700 may control medical devices of the hospital room to enhance a user sleep state or sleep environment. Further, when the user is located in a living room, the electronic device 1700 may control a television or an air-conditioner of a living room to enhance a user sleep state or sleep environment.

Alternatively, the electronic device 1700 may provide a function for enhancing a user sleep state or sleep environment.

FIGS. 18 to 20 are diagrams illustrating an electronic device including a sleep enhancement function according to an example embodiment of the present disclosure.

Figure 18B:
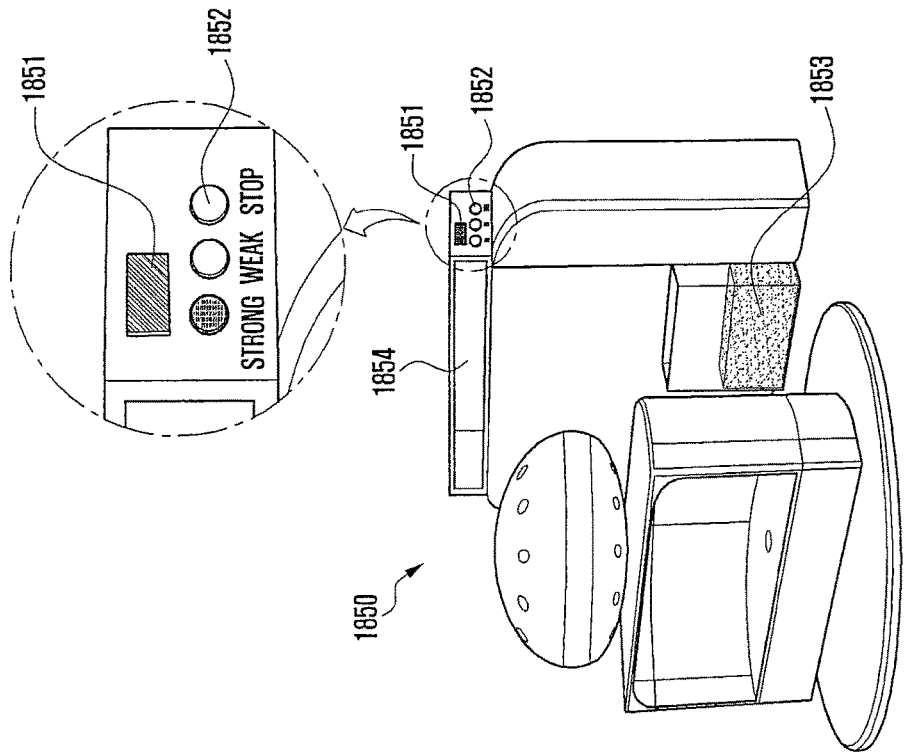
FIG. 18A, FIG. 18B, FIG. 19A, FIG. 19B, FIG. 20A and FIG. 20B are diagrams illustrating an electronic device including a sleep enhancement function according to an example embodiment of the present disclosure.
Figure 18A:
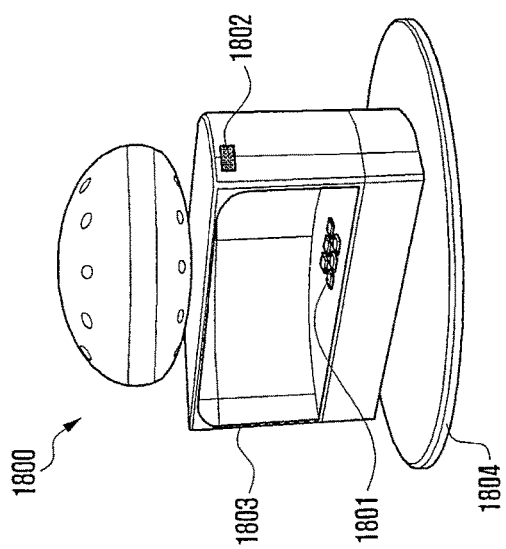

FIG. 18A is a diagram illustrating an electronic device including a lighting function according to an example embodiment of the present disclosure.

With reference to FIG. 18A, an electronic device 1800 may include a light emitting unit (e.g., LED) 1801, illumination sensor 1802, light regulator 1803, rotation plate 1804, and motor (not shown) that can provide lighting to the user.

For example, the electronic device 1800 may include a red light emitting unit and a blue light emitting unit.

In this case, if the user is in a hypnagogic state, the electronic device 1800 may emit red light toward the user using the red light emitting unit.

The electronic device 1800 may adjust a light emitting time and light emitting intensity. For example, the electronic device 1800 may gradually reduce light emitting intensity according to a preset timer.

Alternatively, the electronic device 1800 may rotate the light regulator 1803 by driving a motor (not shown) to adjust light intensity toward a specific area. Specifically, transparency, a thickness, or a perforating level of a circumferential surface of the light regulator 1803 may be different. In this case, the electronic device 1800 may rotate the light regulator 1803 in consideration of a property of the circumferential surface to adjust intensity of light toward a specific area.

In another example, when a user wake-up time (or alarm time) has come, the electronic device 1800 may emit blue light toward a user using the blue light emitting unit.

Even in this case, the electronic device 1800 may adjust a light emitting time and light emitting intensity. For example, the electronic device 1800 may gradually reduce or increase light emitting intensity according to a preset timer.

In particular, the electronic device 1800 may intensify provision of lighting toward a person's face portion based on image information or a movement of a person.

Further, when different wake-up times are set on a basis of a plurality of users, the electronic device 1800 may detect a face portion of each of the plurality of users. The electronic device 1800 may selectively provide lighting toward a face portion of a user related to a predetermined wake-up time at every predetermined time.

If the user wakes up, the electronic device 1800 may automatically turn off any lighting that is emitting light.

According to various example embodiments, if a user sleep posture is not good, the electronic device 1800 may emit light such that the user adopts a correct sleep posture. In this case, in order to avoid light, the user may change unconsciously a posture. A light emitting function may be performed as an option according to a user selection.

FIG. 18B is a diagram illustrating an electronic device including a humidification function according to an example embodiment of the present disclosure.

With reference to FIG. 18B, in order to provide a humidification function, an electronic device 1850 may include a humidity sensor 1851, humidity regulator 1852, water container 1853 that stores water, vapor discharge unit 1854, and motor (not shown).

For example, while rotating by driving a motor (not shown), the electronic device 1850 may discharge a vapor vaporized at the water container 1853 through the vapor discharge unit 1854.

Further, if the user is in a hypnagogic stage, the electronic device 1850 may measure humidity of a sleep environment using the humidity sensor 1851. In order to provide humidity of an optimal sleep state to the user based on humidity of a sleep environment, the electronic device 1850 may provide a humidification function.

Figure 19A:
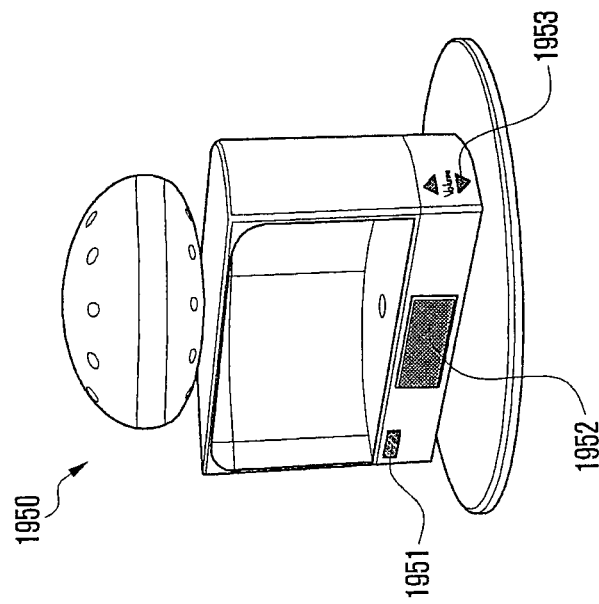

FIG. 19A is a diagram illustrating an electronic device including an air purification function according to an example embodiment of the present disclosure.

With reference to FIG. 19A, in order to provide an air purification function, an electronic device 1900 may include an air quality sensor 1901, filter unit (e.g., carbon filter, nonwoven fabric, high-efficiency particulate air "HEPA" filter) 1902, and air discharge unit 1903.

In this case, if a user is in a hypnagogic stage, the electronic device 1900 may increase rotation strength of a motor to provide purified air. If an air quality is in a state optimal to sleep based on a sensing value of the air quality sensor 1901, in order to reduce motor noise, the electronic device 1900 may lower rotation strength of the motor.

Further, the electronic device 1900 may detect a user movement. In this case, in order to purify air of a user face portion based on the detected user movement, the electronic device 1900 may perform an air purification function.

Figure 19B:
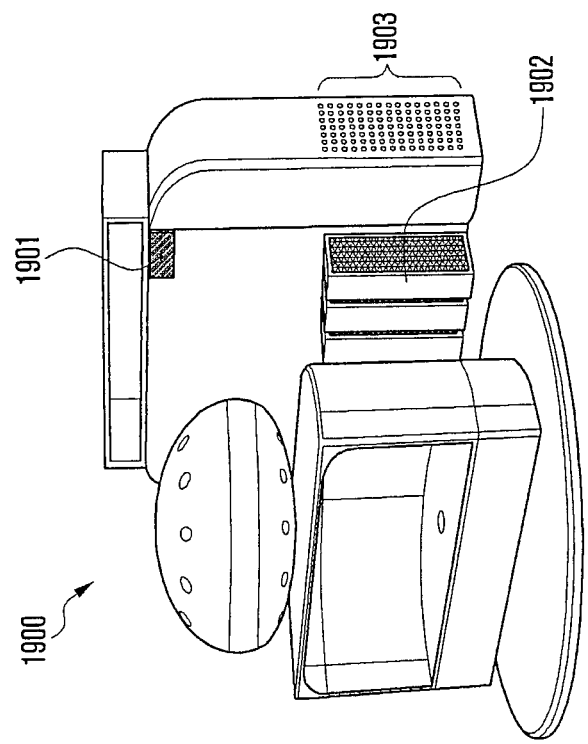

FIG. 19B is a diagram illustrating an electronic device including a sound function according to an example embodiment of the present disclosure.

With reference to FIG. 19B, in order to provide a sound to the user, an electronic device 1950 may include a noise sensor 1951, speaker 1952, and volume adjustment button 1953.

For example, if a user is in a hypnagogic stage, the electronic device 1950 may provide a sound (e.g., music) through the speaker 1952. Alternatively, a sound providing time may be previously determined by user setup or by setting to a default time.

Further, the electronic device 1950 may adjust a sound providing time or a sound volume based on a user movement. For example, when a user movement becomes less, the electronic device 1950 determines that a user is falling asleep and may reduce a sound providing time or a sound volume. Further, the electronic device 1950 may provide a sound of a greater intensity in a direction in which the user is located based on a user movement.

Further, when a user wake-up time has come, the electronic device 1950 may automatically provide a sound. In this case, the electronic device 1950 may provide a sound at a predetermined time before providing an alarm previously set by the user. If the user wakes up, the electronic device 1950 may automatically turn off a sound.

Further, the electronic device 1950 may automatically adjust a kind of a sound and a volume of a sound according to a user sleep stage (e.g., deep sleep, light sleep, REM sleep).

Figure 20A:
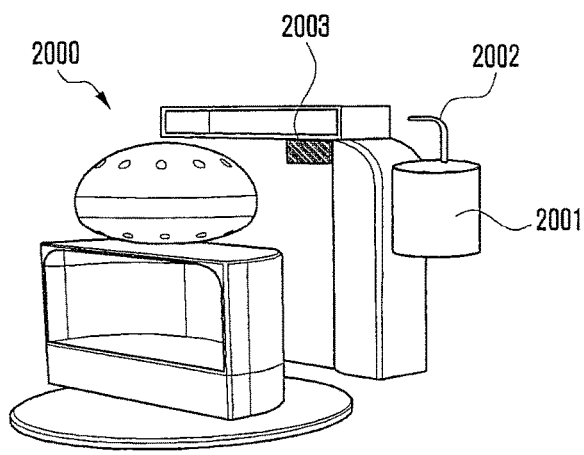

FIG. 20A is a diagram illustrating an electronic device including an oxygen supply function according to an example embodiment of the present disclosure.

With reference to FIG. 20A, in order to supply oxygen, an electronic device 2000 may further include an oxygen generator 2001, sprayer 2002, and $CO_2$ measurement sensor 2003.

For example, if a user wakes up, the electronic device 2000 may control an oxygen generator to increase an oxygen generation amount such that the user experiences a comfortable feeling upon waking up.

Further, the electronic device 2000 may automatically determine a user wake-up to turn on or off the oxygen generator. Further, the electronic device 2000 may adjust an oxygen generation amount based on a $CO_2$ amount around a user detected by the $CO_2$ measurement sensor 2003. For example, if a $CO_2$ amount is a threshold value or more, the electronic device 2000 may turn on the oxygen generator or may increase an oxygen generation amount. If a $CO_2$ amount is less than a threshold value, the electronic device 2000 may turn off the oxygen generator or may reduce an oxygen generation amount.

Figure 20B:
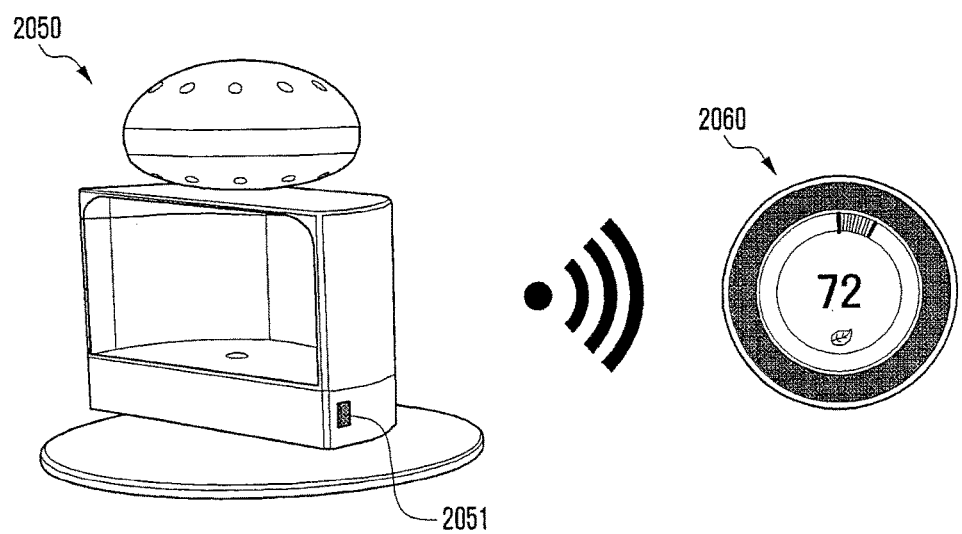

FIG. 20B is a diagram illustrating an electronic device including a temperature adjustment function according to an example embodiment of the present disclosure.

With reference to FIG. 20B, an electronic device 2050 may include a temperature sensor 2051.

The electronic device 2050 may transmit a control signal to a thermostat 2060 within a house to maintain a temperature (e.g., 18° C. to 22° C.) optimized to a sleep.

For example, if a temperature value detected by the temperature sensor 2051 is a threshold value or more or a threshold value or less, the electronic device 2050 may transmit a control signal to the thermostat 2060 through a communication unit (not shown). The thermostat 2060 may lower or increase a temperature within a house based on the received control signal.

Figure 21:
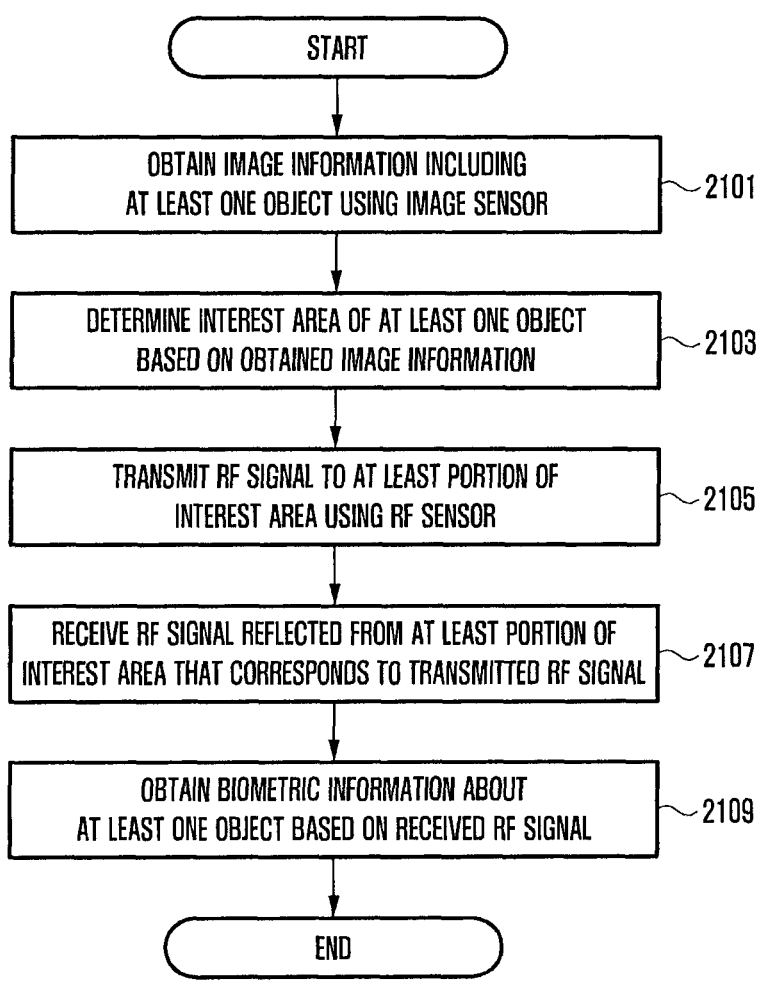
FIG. 21 is a flowchart illustrating a process in which an electronic device obtains biometric information according to an example embodiment of the present disclosure.

FIG. 21 is a flowchart illustrating a process in which an electronic device obtains biometric information according to an example embodiment of the present disclosure.

The electronic device may obtain image information including at least one object using an image sensor at operation 2101.

The electronic device may determine at operation 2103 an interest area of at least one object based on the obtained image information.

For example, at least one object may include a first object and a second object, and the electronic device may determine each of a first interest area about the first object and a second interest area about the second object. Further, the electronic device may determine an interest area based on at least one of a user sleep posture, a user clothing wearing state, a kind of a body portion, and a designated interest area history.

The electronic device may transmit an RF signal to at least a portion of an interest area using the RF sensor at operation 2105.

The electronic device may receive an RF signal reflected from at least a portion of the interest area that corresponds to the transmitted RF signal at operation 2107.

The electronic device may obtain biometric information at operation 2109 about at least one object based on the reflected and received RF signal. For example, the electronic device may obtain movement information according to a change of the interest area based on the received RF signal and obtain biometric information about at least one object based on obtained movement information. Further, when both of a first interest area of the first object and a second interest area of the second object are determined, the electronic device may obtain both of first biometric information about the first interest area and second biometric information about the second interest area.

According to various example embodiments, the electronic device may store image information, a received RF signal value, movement information about an interest area obtained based on a received RF signal, and biometric information obtained based on the movement information at a security area.

According to various example embodiments, when a portion of information stored at a security area is information of a first level, the electronic device may change the information of a first level to information of a second level of a high security level and transmit the information of the second level to an external device.

According to various example embodiments, when at least one object includes a first object and a second object and when the first object is in an abnormal situation, the electronic device may re-obtain biometric information about the first object among the first object and the second object for a designated time.

According to various example embodiments, when at least one object includes a first object and a second object and when the first object is in an abnormal situation, the electronic device may obtain image information including the first object using an image sensor.

Figure 22:
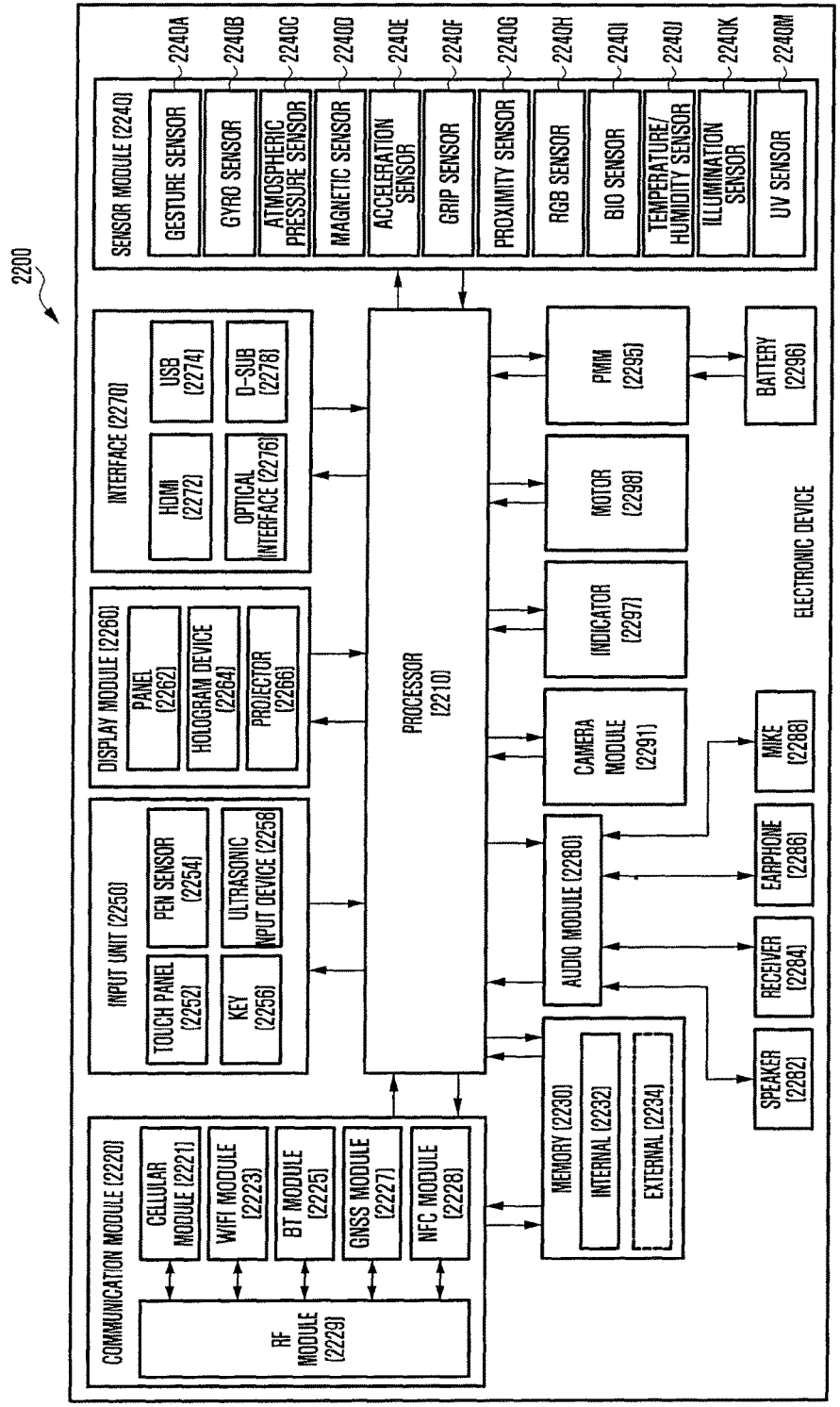
FIG. 22 is a block diagram illustrating a device according to an example embodiment of the present disclosure.

FIG. 22 is a block diagram illustrating a configuration of a device according to an example embodiment of the present disclosure.

The entire or a portion of a device 2200 of FIG. 22 may correspond to an electronic device or an external device of the present disclosure.

For example, the device 2200 of FIG. 22 is an electronic device of the present disclosure and may correspond to each of 100 of FIG. 1, 200 of FIG. 2, 300 of FIG. 3, 400 of FIG.

4, 1300 of FIG. 13A, FIG. 13B and FIG. 13C, 1400 of FIG. 14A and FIG. 14B, 1700 of FIG. 17, 1800 and 1850 of FIG. 18A and FIG. 18B, 1900 and 1950 of FIGS. 19A and 19B, and 2000 and 2050 of FIGS. 20A and 20B. Further, the device 2200 of FIG. 22 is an external device of the present disclosure and may correspond to each of 110 of FIG. 1, 1450 of FIGS. 14A and 14B, and 1550 of FIGS. 15A and 15B.

The device 2200 of FIG. 22 may include at least one processor (e.g., AP) 2210, communication module 2220, memory 2230, sensor module 2240, input device 2250, display 2260, interface 2270, audio module 2280, camera module 2291, power management module 2295, battery 2296, indicator 2297, and motor 2298.

The processor 2210 may correspond to the processor 211 of FIG. 2 and the processor 410 of FIG. 4.

By driving, for example, an operation system or an application program, the processor 2210 may control a plurality of hardware or software components connected thereto and perform various data processing and calculation. The processor 2210 may be implemented into, for example, a system on chip (SoC). According to an example embodiment, the processor 2210 may further include a graphic processing unit (GPU) and/or an image signal processor. The processor 2210 may include at least a portion (e.g., a cellular module 2221) of constituent elements of FIG. 2. The processor 2210 may load and process a command or data received from at least one of other constituent elements (e.g., a nonvolatile memory) at a volatile memory and store result data at the nonvolatile memory.

The communication module 2220 may correspond to the communication unit 430 of FIG. 4.

The communication module 2220 may include, for example, a cellular module 2221, WiFi module 2223, Bluetooth (BT) module 2225, global navigation satellite system (GNSS) module 2227, near field communication (NFC) module 2228, and radio frequency (RF) module 2229. The cellular module 2221 may provide, for example, audio dedicated communication, audiovisual communication, a text service, or an Internet service through a communication network. According to an example embodiment, the cellular module 2221 may perform at least a partial function of functions in which the processor 2210 may provide. According to an example embodiment, the cellular module 2221 may include a communication processor (CP). According to an example embodiment, at least a portion (e.g., two or more) of the cellular module 2221, the WiFi module 2223, the BT module 2225, the GNSS module 2227, and the NFC module 2228 may be included in one integrated chip (IC) or an IC package. The RF module 2229 may transmit and receive, for example, a communication signal (e.g., an RF signal). The RF module 2229 may include, for example, a transceiver, power amp module (PAM), frequency filter, low noise amplifier (LNA), or antenna. According to various example embodiments, at least one of the cellular module 2221, WiFi module 2223, BT module 2225, GNSS module 2227, and NFC module 2228 may transmit and receive an RF signal through a separate RF module.

The memory 2230 may correspond to the memory 212 of FIG. 2 and the memory 420 of FIG. 4.

The memory 2230 may include, for example, an internal memory 2232 or an external memory 2234. The internal memory 2232 may include at least one of, for example, a volatile memory (e.g., dynamic read-only memory (DRAM), static read-only memory (SRAM), or synchronous dynamic read-only memory (SDRAM)), nonvolatile memory (e.g., one time programmable ROM (OTPROM), programmable read-only memory (PROM), erasable programmable read only memory (EPROM), electrically erasable and programmable read only memory (EEPROM), mask ROM, flash ROM, flash memory, hard drive, and solid state drive (SSD). The external memory 2234 may include a flash drive, for example, compact flash (CF), secure digital (SD), Micro-SD, Mini-SD, extreme digital (xD), multimedia card (MMC), or memory stick.

The sensor module 2240 may correspond to the sensor unit 440 of FIG. 4.

The sensor module 2240 may measure, for example, a physical quantity or detect an operation state of the device 2200 and convert measured or detected information to an electric signal. The sensor module 2240 may include at least one of, for example, a gesture sensor 2240A, gyro sensor 2240B, atmospheric pressure sensor 2240C, magnetic sensor 2240D, acceleration sensor 2240E, grip sensor 2240F, proximity sensor 2240G, color sensor 2240H (e.g., Red, Green, and Blue (RGB) sensor), biological sensor 2240I, temperature/humidity sensor 2240J, illumination sensor 2240K, and ultraviolet (UV) sensor 2240M. Additionally or alternatively, the sensor module 2240 may include, for example, an e-nose sensor, electromyograph (EMG) sensor, electroencephalogram (EEG) sensor, electrocardiogram (ECG) sensor, infrared (IR) sensor, iris sensor, and/or fingerprint sensor. The sensor module 2240 may further include a control circuit for controlling at least one sensor that belongs therein. In an example embodiment, the device 2200 further includes a processor configured to control the sensor module 2240 as a portion of the processor 2210 or separately from the processor 2210, and when the processor 2210 is in a sleep state, the processor 2210 may control the sensor module 2240.

The input device 2250 may include, for example, a touch panel 2252, (digital) pen sensor 2254, key 2256, or ultrasonic wave input device 2258. The touch panel 2252 may use at least one method of, for example, capacitive, resistive, infrared ray, and ultrasonic wave methods. The touch panel 2252 may further include a control circuit. The touch panel 2252 may further include a tactile layer to provide a tactile response to a user. The (digital) pen sensor 2254 may be, for example, a portion of a touch panel or may include a separate recognition sheet. The key 2256 may include, for example, a physical button, optical key, or key pad. The ultrasonic wave input device 2258 may detect ultrasonic waves generated in an input instrument through a microphone (e.g., microphone 2288) or the microphone 450 of FIG. 4 to determine data corresponding to the detected ultrasonic wave.

The display 2260 may include a panel 2262, hologram device 2264, projector 2266, and/or control circuit for controlling them. The panel 2262 may be implemented with, for example, a flexible, transparent, or wearable method. The panel 2262 and the touch panel 2252 may be formed in at least one module. According to an example embodiment, the panel 2262 may include a pressure sensor (or a force sensor) that can measure pressure strength of a user touch. The pressure sensor may be integrally implemented with the touch panel 2252 or may be implemented into at least one sensor separate from the touch panel 2252. The hologram device 2264 may show a stereoscopic image in the air using interference of light. The projector 2266 may project light on a screen to display an image. The interface 2270 may include, for example, a High Definition Multimedia Interface (HDMI) 2272, Universal Serial Bus (USB) 2274, optical interface 2276, or D-subminiature (D-sub) 2278. Additionally or alternatively, the interface 2270 may include, for example, a Mobile High-definition Link (MHL) interface, Secure Digital (SD) card/Multi-Media Card (MMC) interface, or Infrared Data Association (IrDA) specification interface.

The audio module 2280 may bilaterally convert, for example, a sound and an electric signal. The audio module 2280 may process sound information input or output through, for example, a speaker 2282 (e.g., the speaker of FIG. 4), receiver 2284, earphone 2286, or microphone 2288.

The camera module 2291 may correspond to the camera 220 of FIG. 2.

The camera module 2291 may photograph a still picture and a moving picture and include at least one image sensor (e.g., a front surface lens or a rear surface lens), a lens (not shown), an Image Signal Processor (ISP), or a flash (e.g., a Light Emitting diode (LED) or a xenon lamp) according to an example embodiment. The power management module 2295 may manage power of the device 2200. According to an example embodiment, the power management module 2295 may include a Power Management Integrated Circuit (PMIC), charger integrated circuit (IC), battery, or fuel gauge. The PMIC may have a wire and/or wireless charge method. The wireless charge method may include, for example, a magnetic resonance method, magnetic induction method, or electromagnetic wave method and may further include an additional circuit, for example, a coil loop, resonant circuit, and rectifier for wireless charge. The battery gauge may measure, for example, a residual quantity of the battery 2296, a voltage, a current, or a temperature while charging. The battery 2296 may include, for example, a rechargeable battery and/or a solar battery.

The indicator 2297 may display a specific state, for example, a booting state, a message state, or a charge state of the device 2200 or a portion (e.g., the processor 2210) thereof.

The motor 2298 may convert an electric signal to a mechanical vibration and generate a vibration or a haptic effect.

The elements each described in the present disclosure may be configured with at least one component, and a name of a corresponding element may be changed according to a kind of the electronic device.

In various example embodiments, some constituent elements of the device 2200 may be omitted, the device 2200 may further include an additional constituent element, or some constituent elements may be coupled to configure one entity, thereby performing an operation according to the present disclosure.

Disclosed example embodiments may be implemented into a software program including an instruction stored at a computer readable storage medium.

A computer is a device that calls a stored instruction from a storage medium and that may operate by the called instruction according to disclosed example embodiments and may include an electronic device or an external device according to disclosed example embodiments.

For example, the computer is an electronic device of the present disclosure and may correspond to each of 100 of FIG. 1, 200 of FIG. 2, 300 of FIG. 3, 400 of FIG. 4, 1300 of FIG. 13A, FIG. 13B and FIG. 13C, 1400 of FIG. 14A and FIG. 14B, 1700 of FIG. 17, 1800 and 1850 of FIG. 18A and FIG. 18B, 1900 and 1950 of FIG. 19A and FIG. 19B, and 2000 and 2050 of FIG. 20A and FIG. 20B. Further, the computer is an external device of the present disclosure and may correspond to each of 110 of FIG. 1, 1450 of FIG. 14A and FIG. 14B, and 1550 of FIGS. 15A and 15B.

A computer readable storage medium may be provided in a format of a non-transitory storage medium. Here, "non-transitory" means that a storage medium does not include a signal and is tangible and does not divide and that data are semi-permanently or temporarily stored at a storage medium.

Further, a method according to disclosed example embodiments may be provided to a computer program product.

The computer program product may include a software program or a computer readable storage medium in which a software program is stored. For example, the computer program product may include a software program electronically distributed through an electronic market or directly distributed by a production company of an electronic device and an external device of the present disclosure. In this case, at least a portion of the software program may be temporarily generated at a storage medium (e.g., a server or a relay server of an electronic market) for electronic distribution. In such a case, a storage medium that stores at least a portion of a temporarily generated software program may be a computer readable storage medium of the present disclosure.

According to the present disclosure, an electronic device can monitor a user using both an image sensor and an RF sensor.

For example, while the user sleeps, the electronic device can unconsciously and remotely obtain biometric information according to a user movement change using the image sensor and the RF sensor.

The electronic device or an external device connected to the electronic device by communication means can provide a sleep management service such that a user sleeps or wakes up in an optimal environment using the obtained biometric information.

Further, the electronic device can provide an air purification function, humidification function, lighting function, sound providing function, or oxygen supply function such that a user sleeps in an optimal environment.

In addition, effects that may be obtained or estimated because of an example embodiment of the present disclosure have been directly or implicitly described in a detailed description of an example embodiment of the present disclosure. For example, various effects estimated according to an example embodiment of the present disclosure have been described in a detailed description.

Although example embodiments of the present disclosure have been described in detail hereinabove it should be clearly understood that many variations and modifications of the basic inventive concepts herein described that may appear to those skilled in the art will still fall within the example embodiments of the present disclosure as defined in the appended claims.

What is claimed is:

1. An electronic device, comprising:
   an image sensor;
   a radio frequency (RF) sensor including a transmitting circuit and a receiving circuit; and
   a processor configured to:
   capture an image including at least one object using the image sensor,
   determine an interest area of the at least one object included within the captured image,
   transmit an RF signal to at least a portion of the interest area using the transmitting circuit,
   receive the transmitted RF signal when the transmitted RF signal is reflected from the at least the portion of the interest area using the receiving circuit, and obtain biometric information for the at least one object based on the reflected RF signal.

2. The electronic device of claim 1, wherein the processor is configured to detect movement of the at least one object when detecting a change in the interest area based on the reflected RF signal; and wherein the biometric information is obtained based at least in part on the detected movement.

3. The electronic device of claim 2, further comprising a memory including at least one security area for storing secured information, wherein the processor is configured to store the captured image, the reflected RF signal value, the detected movement, and/or the obtained biometric information in the at least one security area.

4. The electronic device of claim 3, wherein information stored on the electronic device is classified into a plurality of security levels including a first security level and a second security level, and wherein information stored in the security area is changed from the first security level to the second security level when the stored information is transmitted to an external device.

5. The electronic device of claim 1, wherein the at least one object comprises a first object and a second object, and wherein the processor is configured to determine a first interest area for the first object and a second interest area for the second object.

6. The electronic device of claim 5, wherein the processor is configured to obtain first biometric information based on the first interest area, and second biometric information based on the second interest area.

7. The electronic device of claim 1, wherein the at least one object includes a body of a user, and wherein the processor is configured to determine the interest area based on a sleep posture of the user, a presence of clothing worn by the user, a portion of the user's body, and/or a predesignated interest area.

8. The electronic device of claim 1, wherein the at least one object comprises a first object and a second object, and wherein, when biometric information about the first object cannot be obtained, the processor is configured to re-obtain the biometric information for the first object from among the first object and the second object for a predesignated time.

9. The electronic device of claim 8, further comprising a memory, wherein, when biometric information about the first object cannot be obtained, the processor is configured to capture a second image of the first object using the image sensor, and store the captured second image in the memory.

10. The electronic device of claim 1, wherein the biometric information comprises sleep state information of a user of the electronic device.

11. The electronic device of claim 1, wherein when the at least one object includes a body of a user of the electronic device, the interest area includes a portion of a body of the user, the portion including at least one of a face, a chest, a head, a back, or an abdomen.

12. A method in an electronic device, the method comprising:

capturing an image including at least one object using an image sensor;

determining an interest area of the at least one object included within the captured image;

transmitting a radio frequency (RF) signal to at least a portion of the interest area using an RF sensor;

receiving the transmitted RF signal reflected from the at least the portion of the interest area using the RF sensor; and obtaining biometric information for the at least one object based on the reflected RF signal.

13. The method of claim 12, further comprising:

detecting movement of the at least one object when detecting a change in the interest area based on the reflected RF signal, wherein the biometric information is obtained based at least in part on the detected movement.

14. The method of claim 12, wherein the electronic device includes a memory including at least one security area for storing secured information, the method further comprising:

storing the captured image, the reflected RF signal value, the detected movement, and/or the obtained biometric information in the at least one security area.

15. The method of claim 14, wherein information stored on the electronic device is classified into a plurality of security levels including a first security level and a second security level, and wherein information stored in the security area is changed from the first security level to the second security level when the stored information is transmitted to an external device.

16. The method of claim 12, wherein the at least one object comprises a first object and a second object, and wherein determining an interest area of the at least one object based on the image information comprises determining a first interest area for the first object and a second interest area for the second object.

17. The method of claim 16, further comprising obtaining first biometric information based on the first interest area and second biometric information based on the second interest area.

18. The method of claim 12, wherein the at least one object comprises a first object and a second object, and wherein, when biometric information about the first object cannot be obtained, the method further comprises re-obtaining the biometric information for the first object from among the first object and the second object for a predesignated time.

19. The method of claim 12, wherein the at least one object comprises a first object and a second object, and wherein, when biometric information about the first object cannot be obtained, the processor is configured to capture a second image of the first object using the image sensor, and store the captured second image in memory.

20. A non-transitory computer readable recording medium comprising instructions executable by a processor to cause the processor to perform operations including:

capturing an image including at least one object using an image sensor;

determining an interest area of the at least one object included within the captured image;

transmitting a radio frequency (RF) signal to at least a portion of the interest area using an RF sensor;

receiving the transmitted RF signal reflected from the at least the portion of the interest area using the RF sensor; and obtaining biometric information for the at least one object based on the reflected RF signal.

* * * * *